United States Patent
Rommelspacher

(10) Patent No.: US 9,107,914 B2
(45) Date of Patent: Aug. 18, 2015

(54) BETA-CARBOLINES FOR USE IN THE TREATMENT OF HEARING LOSS AND VERTIGO

(75) Inventor: Hans Rommelspacher, Berlin (DE)

(73) Assignee: AudioCure Pharma GmbH, Berlin (DE)

( * ) Notice: Subject to any disclaimer, the term of this patent is extended or adjusted under 35 U.S.C. 154(b) by 209 days.

(21) Appl. No.: 13/514,171

(22) PCT Filed: Dec. 28, 2010

(86) PCT No.: PCT/DE2010/001530
§ 371 (c)(1),
(2), (4) Date: Oct. 17, 2012

(87) PCT Pub. No.: WO2011/079841
PCT Pub. Date: Jul. 7, 2011

(65) Prior Publication Data
US 2013/0028958 A1    Jan. 31, 2013

Related U.S. Application Data

(60) Provisional application No. 61/282,395, filed on Feb. 2, 2010.

(30) Foreign Application Priority Data

Dec. 28, 2009  (DE) .......................... 10 2009 060 811

(51) Int. Cl.
| | | |
|---|---|---|
| *A61K 31/47* | (2006.01) | |
| *C07D 471/04* | (2006.01) | |
| *A61K 31/437* | (2006.01) | |
| *A61K 9/00* | (2006.01) | |
| *A61K 9/20* | (2006.01) | |

(52) U.S. Cl.
CPC ............. *A61K 31/437* (2013.01); *A61K 9/0046* (2013.01); *A61K 9/2054* (2013.01)

(58) Field of Classification Search
CPC ........................... C07D 471/04; A61K 31/437
USPC .......................................... 546/85; 514/292
See application file for complete search history.

(56) References Cited

U.S. PATENT DOCUMENTS

| 4,731,358 A | 3/1988 | Huth et al. |
| 5,604,236 A | 2/1997 | Jakubowski et al. |
| 2004/0038970 A1 | 2/2004 | Thurieau et al. |
| 2005/0143371 A1* | 6/2005 | Meyers et al. ................ 514/215 |
| 2010/0143474 A1 | 6/2010 | Rommelspacher |

FOREIGN PATENT DOCUMENTS

WO    WO 2008104161 A1 *  9/2008 ........... C07D 471/04

OTHER PUBLICATIONS

Byrn, Stephen. Solid-State Chemistry of Drugs, 2d, Chapter 11 Hydrates and Solvates/hydrates, 233-247, 233.*
Morissette, Sherry. Adv. Drug Delivery Rev. 2004, 56, 275-300.*
Rouhi, A.M. Chem. & Eng. News, Feb. 24, 2003, 81(8), 32-35.*
Hamann, Juliane. Neurochemistry International 52 (2008)688-700.*
Cao, Rihui. Bioorganic & Medicinal Chemistry 12 (2004) 4613-4623.*
Hearing Loss Association of American. Hearing Loss: Types, Causes and Treatment. 2014. <http://www.hearingloss.org/content/types-causes-and-treatment>.*
(Vestibular Disorder Assosiation. Types of Vestibular Disorders. 2014. < http://vestibular.org/understanding-vestibular-disorder/types-vestibular-disorders>.*
MayoClinic. Meniere's Diseases. 20104. < http://www.mayoclinic.org/diseases-conditions/menieres-disease/basics/definition/con-20028251 >.*
WebMD. Brain & Nervous System Health Center. 2013. < http://www.webmd.com/brain/tc/dizziness-lightheadedness-and-vertigo-prevention>.*
International Search Report for PCT Application No. PCT/DE2010/001530, issued Mar. 21, 2011.
International Preliminary Report on Patentability for PCT Application No. PCT/DE2010/001530, issued May 27, 2011.
Liang Xing Qun, et al. "Neurotrophic Factors in the Auditory Periphery" Annals of the New York Academy of Science, vol. 884, pp. 292-304, Nov. 1999.

* cited by examiner

*Primary Examiner* — Golam M M Shameem
*Assistant Examiner* — Laura Daniel
(74) *Attorney, Agent, or Firm* — Meyertons, Hood, Kivlin, Kowert & Goetzel, P.C.; Eric B. Meyertons

(57) ABSTRACT

The present invention is directed at β-carbolines, preferred 9-alkyl-β-carbolines (9-alkyl-β-BC), their manufacture as well as their use in prophylaxis and treatment of hearing damages, tinnitus, acute acoustic trauma, vertigo and vestibular disorder as well as pharmaceutical compositions containing theses β-carbolines.

5 Claims, 13 Drawing Sheets

9-methyl-β-carboline 9-fluoroethyl-β-carboline 6-methoxy-9-methyl-β-carboline

Figure 1:
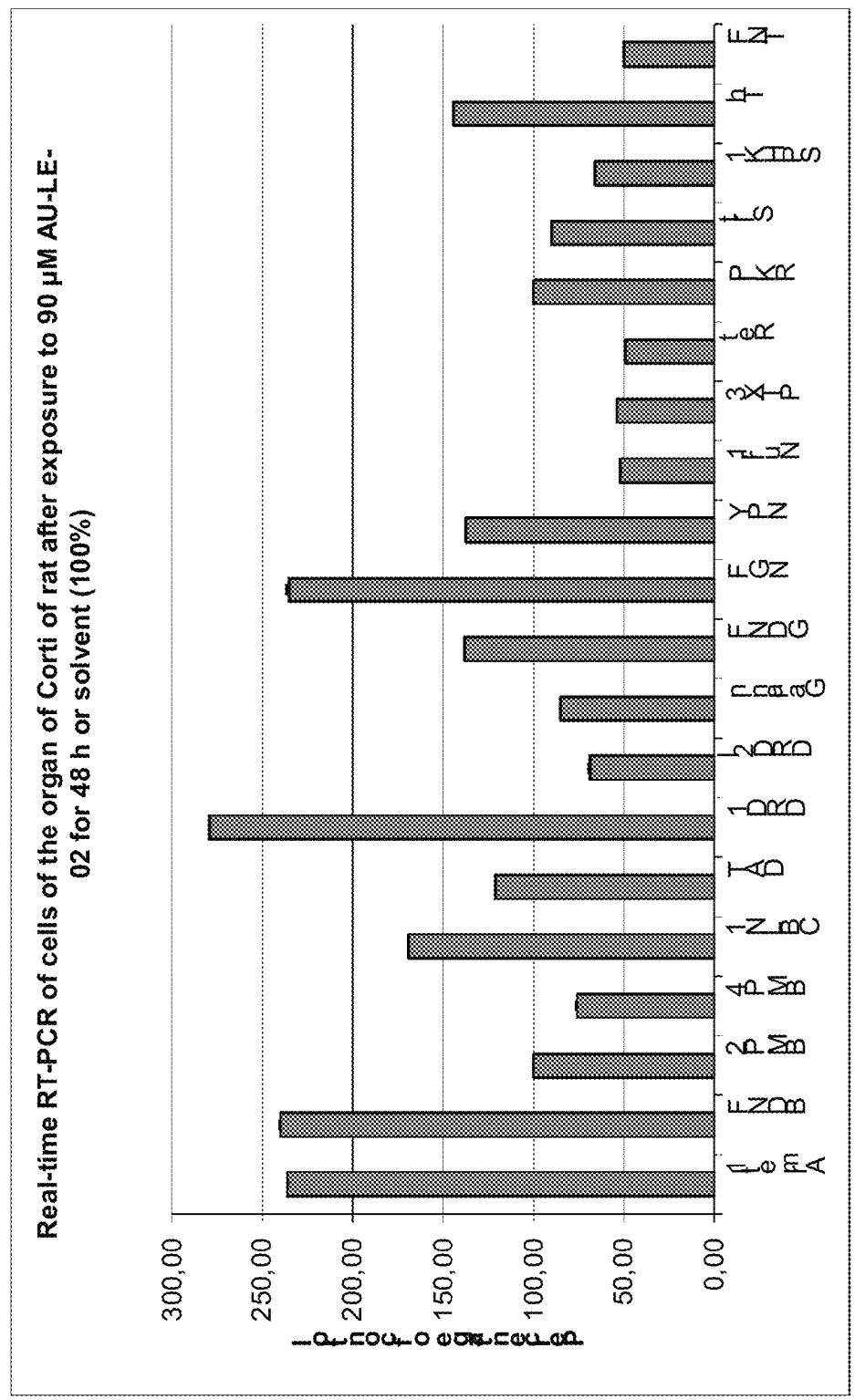

Level of 9-Me-BC in perilymph (1.90 ng / 5 µl) after 3 hours of extra-cochlea infusion Level of 9-Me-BC in perilymph (7.03 ng / 5 µl) after 10 hours of extra-cochlea infusion Level of 9-Me-BC in perilymph (46.0 pg / 5 µl), determined
3 hours after intra-cochlear administration (20 µg)

Level of 9-Me-BC in perilymph (78.8 pg / 5 µl), determined
20 hours after intra-cochlear administration (20 µg)

BETA-CARBOLINES FOR USE IN THE TREATMENT OF HEARING LOSS AND VERTIGO

PRIORITY CLAIM

This application is a 371 of PCT Application PCT/DE2010/001530, filed Dec. 28, 2010, which claims priority to German Patent Application No. 10 2009 060 811.7, filed Dec. 28, 2009 and U.S. Provisional Application Ser. No. 61/282,395, filed Feb. 2, 2010.

The present invention is directed to β-carbolines, preferably 9-alkyl-β-carbolines (9-alkyl-BC), their production as well as their use in prophylaxis and treatment of hearing damages, vertigo and vestibular disorders and pharmaceutical compositions containing these derivatives.

BACKGROUND OF THE INVENTION

The compounds according to the invention serve the treatment of acute and chronic ear disorders and hearing damages, vertigo and vestibular disorders, in particular acute hearing loss, acute acoustic trauma, explosion trauma, labyrinthine deafness due to chronic noise exposure, presbycusia, trauma during implantation of inner ear prosthesis (insertion trauma), vertigo due to diseases of the inner ear, vertigo in relation with and/or as a symptom of Menière's disease, vestibular disorders in relation with and/or as symptom of Menière's disease, tinnitus and hearing damages due to antibiotics and cytostatics.

Approximately 250 million people worldwide suffer from mild or severe hearing damages according to findings of the World Health Organisation (WHO). In the US, thirty to forty millions of people are affected by hearing damages and hearing losses. Costs of treatments account for approximately 50 billion USD annually for the US only. The German Society of People with Impaired Hearing reported for the year 2007 that approximately 19 percent of the German population above the age of 14 suffers from hearing impairments.

The percentage of people with impaired hearing is increasing with increasing age. Hearing impairments in people above the age of 65 come in fourth place of chronically physical impairments after diseases of bones and joints, hypertension and heart diseases. Thirty-seven percent of people between 60 and 69 and 54 percent of septuagenarians and older of the population are affected by hearing impairments. Approximately 12 to 15 millions patients suffer from labyrinthine deafness, and approximately 2.9 million patients suffer from tinnitus in the Federal Republic of Germany.

The term 'Tinnitus aurium' (Latin for 'the ringing of the ears') or tinnitus in its short form describes a symptom or syndrome, too, by which the affected person perceives noises that have no outer perceivable source for other persons. In contrast, the 'objective tinnitus' is based on an outer perceivable or, at least, measurable endogenous sound source. However, objective tinnitus is very rare compared to subjective tinnitus.

Tinnitus is an acoustic perception that is perceived by the patient independently from sounds acting on the ear. This perception is based on an impairment of hearing function of the labyrinth of the inner ear. Therefore, the auditory impression of tinnitus has nothing to do with the sound in the patient's environment. The types of apparent noises, which the patient perceives, are very multifaceted. One summarises the following acoustic impressions among others by the term 'tinnitus':

Buzzing and whistling noises
Sibilating
Random noise
Cracking or knocking

The noise can be invariant in its intensity; it can have, however, a rhythmic pulsating character as well. There is not always a real noise, which causes the same acoustic impressions as does a tinnitus. One should clearly distinguish tinnitus from acoustic hallucinations, too.

Approximately 10 to 20 percent of the population are affected permanently by tinnitus; just fewer than 40 percent detect such an ear noise at least once in a lifetime. Approximately, a third of all elderly people states to perceive an ear noise all the time. The onset of the disease usually lies between the age of 40 to 50, wherein women and men are affected likewise. The number of patients with tinnitus has been rising in industrialised nations of the Western world in particular.

The present invention is based on the problem to provide drugs as well as pharmaceutical formulations, which are suitable for prophylaxis and treatment of hearing damages, presbycusia, vertigo, and vestibular disorders.

The technical teaching of the independent claims solves this problem. Further advantageous embodiments, aspects and details of the invention result from the dependent claims, the description and the examples.

DESCRIPTION

The invention is directed at the use of the compounds of the general formula (I)

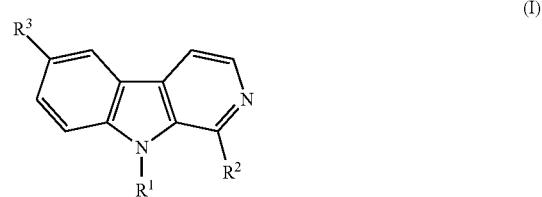

(I)

wherein
$R^1$ stands for one of the following moieties:
—$R^{12}$, —$CR^4R^5R^6$, —$NR^{12}R^{13}$, —CO—NH—$R^{12}$, —CO—O—$R^{12}$;
$R^2$—$R^6$ represent independently of each other the following moieties: —$R^7$, —$R^8$, —$R^9$, —$R^{10}$, —$R^{11}$, —H, —OH, —$OR^7$, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —OPh, —$OCH_2$—Ph, —$OCPh_3$, —SH, —$SCH_3$, —$SC_2H_5$, —$SC_3H_7$, —S-cyclo-$C_3H_5$, —$SCH(CH_3)_2$, —$SC(CH_3)_3$, —$NO_2$, —F, —Cl, —Br, —I, —$N_3$, —CN, —OCN, —NCO, —SCN, —NCS, —CHO, —$COCH_3$, —$COC_2H_5$, —$COC_3H_7$, —CO-cyclo-$C_3H_5$, —COCH$(CH_3)_2$, —$COC(CH_3)_3$, —COOH, —COCN, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —CONH[CH$(CH_3)_2$], —CONH[C$(CH_3)_3$], —CON$(CH_3)_2$, —CON$(C_2H_5)_2$, —CON$(C_3H_7)_2$, —CON(cyclo-$C_3H_5)_2$, —CON[CH$(CH_3)_2]_2$, —CON[C$(CH_3)_3]_2$, —$NHCOCH_3$, —$NHCOC_2H_5$, —$NHCOC_3H_7$, —NHCO-cyclo-$C_3H_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$ —NH—CO—NH$_2$, —NH—CO—NHCH$_3$, —NH—CO—NHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH [C(CH$_3$)$_3$], —NH—CO—N(CH$_3$)$_2$ —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(CH$_3$)$_2$]$_2$, —NH—CO—N [C(CH$_3$)$_3$]$_2$, —NH—CS—NH$_2$, —NH—CS—NHCH$_3$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(CH$_3$)$_2$]$_2$, —NH—CS—N[C(CH$_3$)$_3$]$_2$ —NH—C(=NH)—NH$_2$, —NH—C(=NH)—NHCH$_3$, —NH—C(=NH)—NHC$_2$H$_5$, —NH—C(=NH)—NHC$_3$H$_7$, —OC$_6$H$_4$—OCH$_3$, —NH—C(=NH)—NH-cyclo-C$_3$H$_5$, —NH—C(=NH)—NH[CH(CH$_3$)$_2$], —CF$_2$Cl, —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —OC$_6$H$_4$—CH$_3$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NHC$_3$H$_7$, —O—CO—NH-cyclo-C$_3$H$_5$, —O—CO—NH [CH(CH$_3$)$_2$], —O—CO—NH [C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$—COOH, —CH$_2$—COOCH$_3$, —CH$_2$—COOC$_2$H$_5$, —CH$_2$—COC$_3$H$_7$, —CH$_2$—CO-cyclo-C$_3$H$_5$, —CH$_2$—COCH(CH$_3$)$_2$, —CH$_2$—COC(CH$_3$)$_3$.

R$^7$-R$^{13}$ represent independently of each other the following moieties:

—CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, cyclo-C$_3$H$_5$, cyclo-C$_4$H$_7$, cyclo-C$_5$H$_9$, cyclo-C$_6$H$_{11}$, cyclo-C$_7$H$_{13}$, cyclo-C$_8$H$_{15}$, —Ph, —CH$_2$—Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(OH$_3$)—C$_4$H$_9$, —CH$_2$—CH(OH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —C$_7$H$_{15}$, —C$_8$H$_{17}$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —CH$_2$—CH$_2$—CH=CH—OCH$_3$, —C$_2$H$_4$—CH(CH$_3$)—CH=CH$_2$, —CH$_2$—CH(CH$_3$)—CH$_2$—CH=CH$_2$, —CH$_2$NH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$OH, —CH$_2$SH, —CH$_2$—CH=CH—CH(CH$_3$)$_2$, —CH$_2$—CH=C(CH$_3$)—C$_2$H$_5$, —CH$_2$—CH$_2$—CH$_2$NH$_2$, —CH$_2$—C(CH$_3$)=CH—C$_2$H$_5$, —CH(CH$_3$)—CH=CH—C$_2$H$_5$, —CH$_2$—CH$_2$NH$_2$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH$_2$—CH$_2$SH, —CH(CH$_3$)—CH$_2$—C(CH$_3$)=CH$_2$, —CH(CH$_3$)—CH(CH$_3$)—CH=CH$_2$, —CH$_2$—CH$_2$—CH$_2$OH, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH$_2$—CH$_2$—CH$_2$SH, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —C$_6$H$_4$—OCH$_3$, —CH$_2$—CH=CH—CH$_2$—CH=CH$_2$, —CH=CH—C$_2$H$_4$—CH=CH$_2$, —C$_6$H$_4$—OH, CH$_2$CH=CH—CH=CH$_3$, —CH=CH—CH$_2$—CH=CH—CH$_3$, —CH$_2$—CH$_2$—OCH$_3$, —CH=CH—CH—CH=C$_2$H$_5$, —CH$_2$—CH=CH—C(CH$_3$)=CH$_2$, —CH$_2$—CH$_2$OH, —CH$_2$—CH=C(CH$_3$)—CH=CH$_2$, —CH$_2$—C(CH$_3$)=CH—CH=CH$_2$, —CH$_2$—OCH$_3$, —CH(CH$_3$)—CH=CH—CH=CH$_2$, —CH=CH—CH$_2$—C(CH$_3$)=CH$_2$, —CH=CH—CH(CH$_3$)—CH=CH$_2$, —C(CH$_3$)=CH—CH$_2$—CH=CH$_2$, —CH=CH—CH=CH—CH$_2$, —CH=CH—CH=C(CH$_3$)$_2$, —CH$_2$—C$_6$H$_4$—OCH$_3$, —CH=CH—C(CH$_3$)—CH=CH$_3$, —CH=C(CH$_3$)—CH=CH—CH$_3$, —CH$_2$—C$_6$H$_4$—OH, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—

CH═CH$_2$, CH—CH═CH—CH═CH—CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —C$_2$H$_4$—CH(CH$_3$)—C≡CH, —CH$_2$—CH(CH$_3$)—CH$_2$—C≡CH, —CH$_2$—C≡C—CH(CH$_3$)$_2$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —C≡C—CH(CH$_3$)—C$_2$H$_5$, —C≡C—CH$_2$—CH(CH$_3$)$_2$, —CH(C$_2$N—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH$_3$, —CH$_2$—CH(C≡CH)$_2$, —CH (C≡CH)—C≡C—CH$_3$, —C$_{14}$H$_{29}$, —CH$_2$—CH$_2$—N (CH$_3$)$_2$;

as well as pharmacologic acceptable salts, solvates, hydrates, complex compounds, enantiomers, diastereomers, mixtures of diastereomers, prodrugs, tautomers as well as racemates of the afore-mentioned compounds for prophylaxis and treatment of hearing damages, vertigo and vestibular disorders.

The term 'prodrug' as used herein is defined as a pharmacologic substance that is administered in an inactive or less effective form. After administration, it is metabolised into its active, effective form in the body.

The term 'tautomere' as used herein is defined as an organic substance that can interconvert to its equilibrium isomer by a chemical reaction, tautomerisation. Preferably, bases, acids or other suitable substances can catalyse tautomerisation.

General Synthesis of 9-alkyl-β-carbolines

The starting compound, norharman, can be produced by protocols known in the literature as described in example 1, for example.

In accordance with well-established alkylation reactions, N-alkylation of position 9 results from alkyl iodides, alkyl bromides, alkyl chlorides, alkyl mesylates, alkyl tosylates or other alkylation reagents according the reaction scheme as below:

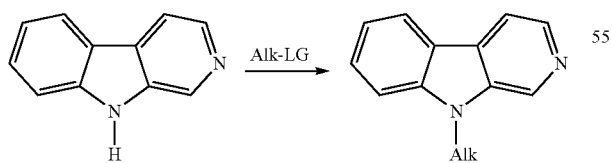

LG stands for a leaving group. Alkylation reactions preferably are base-catalysed.

General Reaction Protocol for Alkylation:

One mol equivalent of norharman is dissolved in a dried solvent such as DMF, THF, methylene chloride etc. under an inert gas atmosphere. Deprotonation results from an excess of strong base, preferably sodium hydride (approximately 2 mol equivalents), at low temperatures (−78° C. to 0° C.). 1.0 to 1.2 mole equivalents of an alkylation reagent, which can be dissolved in a dried solvent, are also added at a temperature below 0° C. One stirs the mixture overnight, whereby the reaction solution can heat itself to room temperature. Processing is performed in a manner known to the skilled person. Non-converted norharman can be removed by ion exchange chromatography or ion pair extraction. Usually, yields are in the range from 30 to 75 percent of the theoretical yield.

The following compounds were synthesised according to the above alkylation.

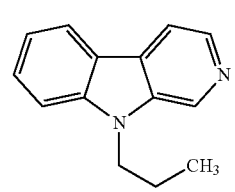

compound A

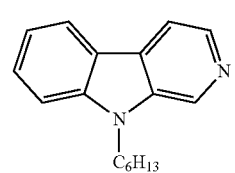

compound B

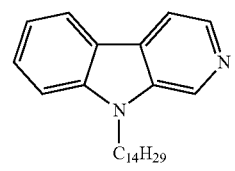

compound C

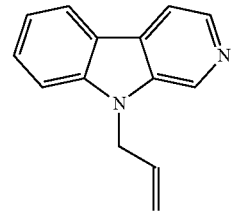

compound D

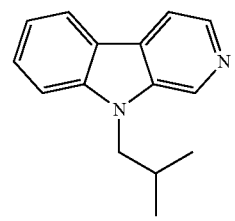

compound E

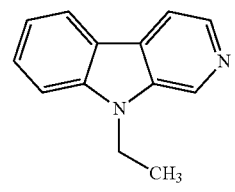

compound F

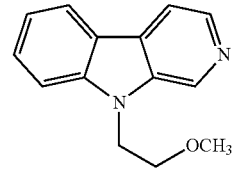

compound G

-continued

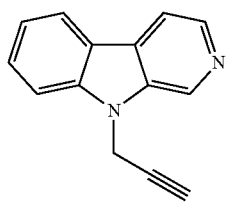
compound H

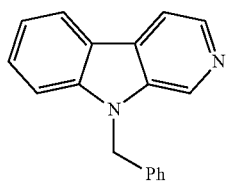
compound I

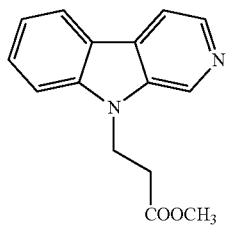
compound J

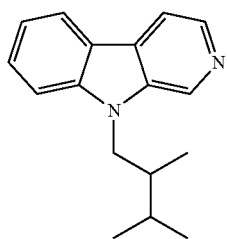
compound K

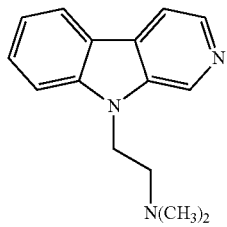
compound L

General Synthesis of 1,6-bi-substituted β-carbolines

Indole derivatives were reacted with the corresponding aldehydes to obtain 1,6-di-substituted β-carbolines according to the above reaction scheme.

Thereby, 0.1 mole of indole derivative was dissolved in DMF and 0.12 mole of the aldehyde was added with stirring. The reaction mixture was stirred at room temperature for 16 hours. After removal of the solvent, the resulting solid was re-crystallised twice in toluene and dried. In a further synthesis step, 0.07 mol of the solid re-crystallised in toluene and dried were dissolved in 600 ml of cumene and reflux-heated with 2.6 grams of Pd/C (10%) in a nitrogen atmosphere for 90 minutes. After addition of 100 ml of ethanol, the hot solution was filtrated, and the coal was extracted three times by 30 ml of hot ethanol. The combined liquid fractions were freed of solvent in vacuum, and the residue was crystallised in toluene to obtain the 1,3-disubstituted derivative of norharman.

If $R^3$ is a hydrogen atom, then the corresponding 1-substituted β-carbolines are obtained.

After ring-closing reaction, N-alkylation of position 9 is conducted by a base, preferably a hydride, and subsequent addition of an alkylation reagent e.g. an alkyl iodide. A detailed protocol is included into the experimental section. The following compounds were synthesised according to this protocol.

The following compounds of the general formulas (II)-(V) and (XXI) are preferred.

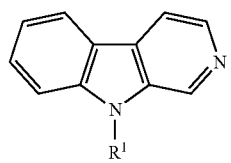
(II)

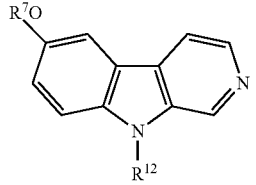
(III)

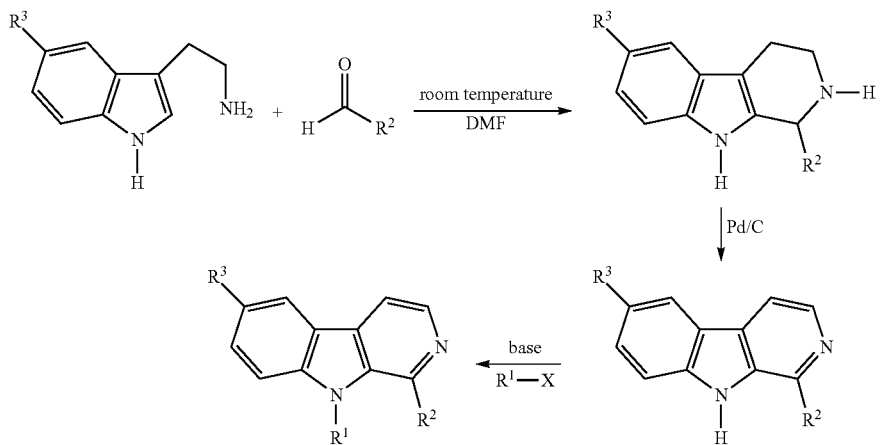

-continued

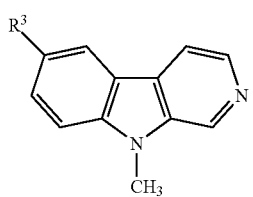
(IV)

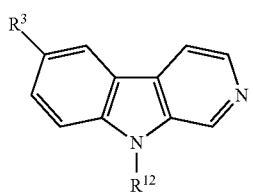
(V)

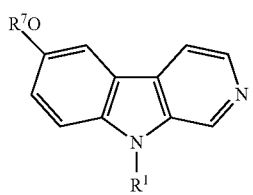
(XXI)

9-Alkyl-β-carbolines according to the invention surprisingly show a pharmacologic effect on hearing damages, vertigo and vestibular disorders as well as other ear diseases, and, thus, are used according to the invention for prophylaxis and treatment of hearing damages, vertigo and vestibular disorder. The indications hearing damages, vertigo and vestibular disorder also comprise particularly labyrinthine deafness, presbycusia, acute hearing loss, hearing loss, trauma during implantation of inner ear prosthesis (insertion trauma), labyrinthine deafness due to chronic noise exposure, acute acoustic trauma, rotational vertigo episodes, nausea and emesis due to hearing damages, vertigo due to diseases of the inner ear, vertigo in relation with and/or as a symptom of Menière's disease, vestibular disorders in relation with and/or as symptoms of Menière's disease, tinnitus and hearing damages due to antibiotics such as penicillines such as penicillin V, propicillin, azidocillin; aminopenicillines such as ampicillin, amoxicillin; cephalosporines such as cefaclor, cefradine; lincomycines such as lincomycin, Clindamycin; tertracyclines such as doxycycline, tetracycline; nitroimidazole such as metronidazole; macrolides such as erythromycin; aminoglycoside such as gentamicin, streptomycin and cytostatics such as actinomycin D, aminoglutethimide, amsacrine, anastrozole, antagonists of purine and pyrimidine bases, anthracyclines, aromatase inhibitors, asparaginase, anti-estrogenes, bexaroten, bleomycine, buselerin, busulfane, camptothecine derivatives, capecitabine, carboplatin, carmustin, chlorambucil, cisplatin, cladribine, cyclophosphamide, cytarabin, cytosinarabinoside, alkylating cytostatics, dacarbazine, dactinomycin, daunorubicin, docetaxel, doxorubicin (adriamycin), epirubicin, estramustin, etoposid, exemestan, fludarabin, fluorouracil, folic acid antagonists, formestan, gemcitabin, glucocorticoides, goselerin, hormones and hormones antagonists, hycamtin, hydroxyurea, idarubicin, ifosfamide, imatinib, irinotecan, letrozole, leuprorelin, lomustin, melphalan, mercaptopurine, methotrexate, miltefosin, mitomycine, mitosis inhibitors, mitoxantrone, nimustine, oxaliplatin, paclitaxel, pentostatin, procarbazin, tamoxifen, temozolomide, teniposide, testolactone, thiotepa, tioguanine, topoisomerase inhibitors, topotecan, treosulfan, tretinoin, triptorelin, trofosfamide, vinblastin, vincristin, vindesin, vinorelbin, cytostatic-effective antibiotics.

The indications, hearing damages and hearing loss, can also be noise-induced and/or are associated with acute acoustic trauma and/or explosion trauma. The most frequently named factors of acoustic trauma, such as acute acoustic trauma or explosion trauma are noise pollution at the workplace and during leisure time.

Tinnitus and hearing damages can also be based on vascular ischaemia, autoimmune disorders, infectious diseases, otosclerosis and cranial trauma. Hence, the present invention is also directed to hearing damages and hearing loss caused by acute acoustic trauma, explosion trauma, noise pollution, vascular ischaemia, autoimmune disorders, infectious diseases, osteoclerosis and cranial trauma.

Vertigo in relation with Menière's disease is an addressable indication according to invention because the inner ear participates in this form of vertigo. This applies to equilibrium dysfunctions, too, because as the vestibular organ the labyrinth is part of the inner ear. Menière's disease or Morbus Menière shows itself in sudden occurring rotational vertigo episodes, nausea, emesis, buzzing in one's ears (Tinnitus aurium) and unilateral hearing loss. Characteristics of this disease, which can occur without recognisable cause at any time day or night, are sudden occurring rotational vertigo together with nausea up to emesis. They last from minutes to hours and will repeat themselves at intervals of different length. Vertigo can be so intense that the patient is not able to stand self-actuating anymore. In addition, there is a fluctuating (temporarily occurring) loss of hearing in relation with ear buzzing (tinnitus) and a pressure feeling in the affected ear.

Substituents at positions 9 ($R^1$) and 6 ($R^3$) of the ring system of β-carboline are preferred. The substitution pattern of $R^1$ preferably comprises alkyl substituents, the methyl substituent particularly preferred. $R^2$ and $R^3$ moieties comprise particularly preferred alkyl substituents, halides and alkoxy substituents. $R^3$ is preferably an alkoxy moiety such as —OCF$_3$, —OCH$_2$—CH$_2$F, —OCH$_2$—CF$_3$, —OCH$_2$—CH$_2$Cl, cyclo-OC$_3$H$_5$, cyclo—OC$_5$H$_9$, cyclo-OC$_6$H$_{11}$, —OPh, —OCH$_2$—Ph, —OCH$_3$, —OC$_2$H$_5$, —OC$_3$H$_7$, —OCH(CH$_3$)$_2$, —OC$_4$H$_9$, —OC$_5$H$_{11}$, —OCH(C$_2$H$_5$)$_2$, —OC$_6$H$_{13}$, —OCH=CH$_2$, —OCH$_2$—CH=CH$_2$, —OC$_7$H$_{15}$, —OC$_8$H$_{17}$, —OCH$_2$—CH=CH—CH$_3$, —OCH$_2$OH, —OCH$_2$—CH$_2$NH$_2$, —OCH$_2$—CH$_2$—CH$_2$OH, —OCH$_2$—CH$_2$—OCH$_3$, —OCH$_2$—CH$_2$OH, —OCH$_2$OCH$_3$, —OCH$_2$—C≡CH.

$R^1$ is preferably an alkyl moiety with up to 6 carbon atoms, further preferred with up to 4 carbon atoms.

The substances 9-methyl-β-carboline and 9-fluoroethyl-β-carboline are particularly preferred.

Preferred compounds are:

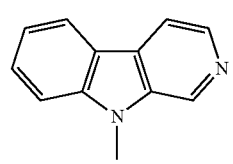
(VI)

9-methyl-9H-β-carboline
(9-Me-BC)

-continued

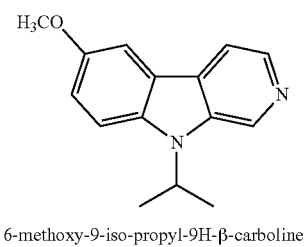

6-methoxy-9-iso-propyl-9H-β-carboline (VII)

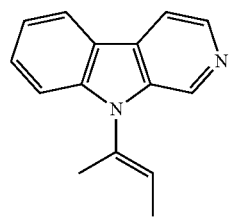

9-[(1Z)-1-methylprop-1-enyl]-9H-β-carboline (VIII)

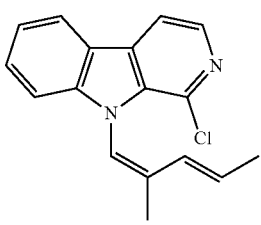

1-chloro-9-[(1Z, 3E)-2-methylpenta-1,3-dienyl]-9H-β-carboline (IX)

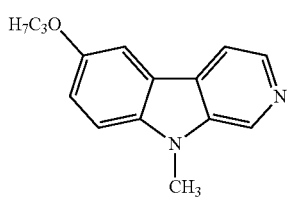

9-methyl-6-propoxy-9H-β-carboline (X)

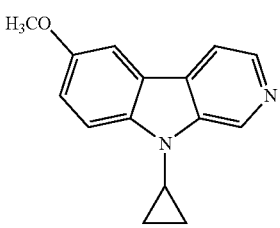

9-cyclopropyl-6-methoxy-9H-β-carboline (XI)

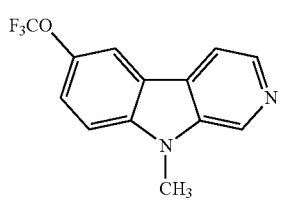

6-trifluoromethoxy-9-methyl-9H-β-carboline (XII)

-continued

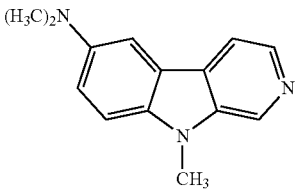

6-dimethylamino-9-methyl-9H-β-carboline (XIII)

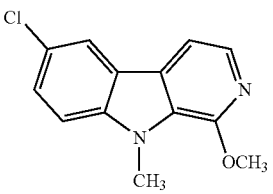

1-methoxy-6-chloro-9-methyl-9H-β-carboline (XIV)

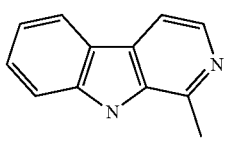

1,9-dimethyl-9H-β-carboline (XV)

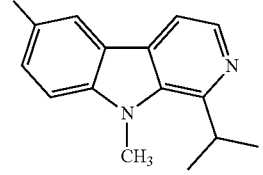

1-isopropyl-6,9-dimethyl-9H-β-carboline (XVI)

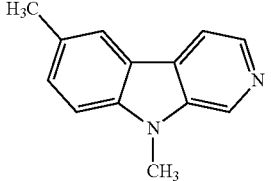

6,9-dimethyl-9H-β-carboline (XVII)

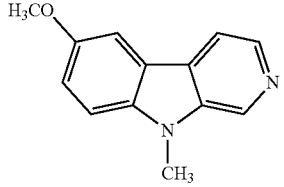

6-methoxy-9-methyl-9H-β-carboline (XVIII)

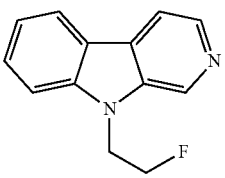

9-(2-fluoroethyl)-9H-β-carboline (XIX)

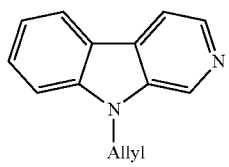

9-allyl-9H-β-carboline

Compounds of the present invention and the particularly preferred compounds of the general formulas (II)-(XX) can be used for the manufacture of a pharmaceutical formulation for the treatment and/or prophylaxis of acute and chronic ear disorders and hearing damages, vertigo and vestibular disorders, in particular acute hearing loss, acute acoustic trauma, labyrinthine deafness due to chronic noise exposure, presbycusia, trauma during implantation of inner ear prosthesis (insertion trauma), vertigo due to diseases of the inner ear, vertigo in relation with and/or as a symptom of Menière's disease, vestibular disorders in relation with and/or as symptom of Menière's disease, tinnitus and hearing damages due to antibiotics and cytostatics.

The compounds according to the present invention can be administered neat or in the form of a pharmacologic effective salt. Because the compounds of the present invention can have alkaline properties, salts of these compounds can be generated by established methods.

The following acids can be listed as acids, which will form an acid addition salt with the compounds of the present invention: sulphuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid (glycon, dextronic acid), lactic acid, malic acid, tartaric acid, dihydroxytartaric acid (hydroxymaleic acid, hydroxypropanoic acid), fumaric acid, citric acid, ascorbic acid, maleic acid, malonic acid, hydroxymaleic acid, pyruvic acid, phenylacetic acid, (o-, m-, p-) toluic acid, benzoic acid, p-aminobenzoic acid, p-hydroxybenzoic acid, salicylic acid, p-aminosalicylic acid, methanesulfonic acid, ethanesulfonic acid, hydroxyethanesulfonic acid, ethylensulfonic acid, p-toluene sulfonic acid, naphthylsulfonic acid, naphthylamino-sulfonic acid, sulfanilic acid, camphorsulfonic acid, quinic acid (quinine acid), o-methyl-mandelic acid, hydrogen benzenesulphonic acid, picric acid (2,4,6-trinitrophenol), adipic acid, d-o-tolyl-tartaric acid, amino acids such as methionine, tryptophane, arginine and, in particular, acidic amino acids such as glutamic acid or asparagic acid.

Betain forms are possible depending on the type of compound.

The present invention further is directed to pharmaceutical compositions, which were manufactured by use of at least one compound according to invention or a salt thereof.

Besides at least one compound of the present invention, the pharmaceutical compositions contain a pharmacologic acceptable carrier, excipient, and/or solvent.

Such formulations are suitable for inhalation or intravenous, intraperitoneal, intramuscular, subcutaneous, mucocutaneous, oral, rectal, transdermal, topical, buccal, intradermal, intragastral, intracutaneous, intranasal, intrabuccal, percutaneous or sublingual administration. Administration or injection into the middle ear as well as topical application to the tympanic membrane is particularly preferred.

The pharmaceutical compositions can be manufactured and administered in form of transdermal application systems (band-aid, film), drops, pills, tablets, film tablets, layer tablets, gels, ointments, syrups, granulates, suppository, emulsions, dispersions, microcapsules, capsules, powders or injection solutions. Pharmaceutical formulations in forms of liposomes, gels, and emulsions are preferred.

The ear is built as following. The acoustic meatus leads from the auricle to the inner of the ear. The acoustic meatus ends at the tympanic membrane. This part of the ear is called the external ear. A room, the so-called middle ear, which is connected to the Eustachian tube, lies behind the external ear. The middle ear is separated by the tympanic membrane on one side and by the oval and round windows on the adjacent side. A room called the inner ear follows behind both windows. The inner ear harbours several organs of the ear, the so-called cochlea among others. This, in turn, contains the organ of Corti. The cochlea as well as the organ of Corti lies next to the round window. Furthermore, the cochlea is connected to the acoustic nerve.

Thus, the membrane of the round window is the biological barrier to the inner ear room and represents the biggest obstacle for local therapy of hearing damages. The applied drug must pass through this membrane to get into the inner ear room. The drug cannot be applied through the membrane mechanically-mechanistically since this will damage the membrane by the manipulation. However, it can be locally delivered to the membrane of the round window in a surgical way, e.g. by injection through the tympanic membrane; and, then, it can penetrate the membrane of the round window. The sensory cells (inner and outer hair cells) of the hearing organ are localised inside the cochlea, and their total number is called the organ of Corti. The hair cells are initially damaged in labyrinthine deafness of any cause (age, drugs such as certain antibiotics and cytostatics) and in tinnitus. The round window finishes off the Scalae tympani and vestibuli, which are compartments within the cochlea. The Scalae tympani and vestibule are filled with perilymph and endolymp so that the hair cells are in direct contact to the perilymph. Therefore, substances, which enter by the round window, are dispersed in the perilymph and will reach the hair cells by this way. In addition, the perilymph system is in contact with the labyrinth. Thereby, drugs also reach the perilymph of the labyrinth, i.e. of the equilibrium organ, via the perilymph of the cochlea.

Hence, all pharmaceutical formulations are preferred, which are suitable to apply the drug locally at the membrane of the round window. It is further preferred if the pharmaceutical formulation contain an enhancer of membrane penetration, which supports the passage of β-carboline through the membrane of the round window. Accordingly, liquid or gel-like formulations are preferred in particular. It is also possible to apply the drug orally of course.

Liquid formulations comprise solutions, suspensions, sprays and emulsions such as injection solutions on water basis or water-propylenglycol basis for parenteral injection.

Low-melting waxes, fatty acid esters, and glycerides are utilised for the preparation of suppositories preferably.

Pharmaceutical compositions, for any kind of administration, contain β-carbolines in a concentration sufficient to achieve a therapeutic effect and, if necessary, inorganic or organic, liquid or solid pharmaceutically acceptable excipients. Pharmaceutical compositions, suitable for topical administration in the middle ear, contain aqueous solutions or suspensions, which can be prepared before administration in the middle ear, such as lyophilized formulations, containing β-carbolines neat or together with an excipient. The pharmaceutical compositions further comprise biodegradable or nonbiodegradable, aqueous or non-aqueous or microspheres based gels. Examples of such gels comprise poloxamers, hyaluronates, xyloglucanes, chitosanes, polyester, polylactide, polyglycolide or co-polymers thereof PLGA, sucrose acetate isobutyrate, glycerol monooleate. Pharmaceutical compositions suitable for enteral or parenteral administration contain tablets or gelatine capsules or aqueous solutions or suspension, as described above.

The pharmaceutical compositions can be sterilized and/or can contain adjuvants, such as preservatives, stabilisers, humectants and/or emulsifiers, salts for regulation of osmotic pressure and/or buffers. The inventive pharmaceutical compositions can, if desired, contain further active substances. The pharmaceutical compositions can be manufactured by any common methods, known from the prior art, such as blending, granulation, confectioning, dissolving and lyophilisation and contain approximately 0.01 to 100 percent, preferably between 0.1 to 50 percent, and as lyophilisates up to 100 percent of β-carbolines.

In a preferred embodiment the inventive pharmaceutical compositions are formulated as topical medications. Suitable excipients for an otogenic medication are organic or inorganic substances that are pharmaceutically acceptable and do not react with β-carbolines and/or any other active substances such as common salt, alcohols, vegetable oils, benzyl alcohol, alkyl glycol, polyethylene glycol, glycerine triacetate, gelatine, carbohydrates such as lactose or starch, magnesium carbonate (magnesia, chalk), stearate (waxes), talc and petrolatum (Vaseline). The described compositions can be sterilized and/or contain adjuvants, such as lubricants, preservatives, such as thiomersal (e.g. 50 weight percent), stabilizers and/or humectants, emulsifiers, salts for regulation of osmotic pressure, buffer substances, colouring agents and/or flavourings. These compositions can also contain, where appropriate, one or several further active substances. Otogenic compositions according to the invention can comprise various substances, containing other biologically active substances, such as antibiotics, anti-inflammatory active substances such as steroids, cortisone, analgesics, antipyrine, benzocaine, procaine etc.

Compositions for topical medication according to the invention can contain other pharmaceutically acceptable substances. In a preferred embodiment of the present invention a topical excipient is used, which does not enhance the release of β-carbolines and possibly of any other active substance or active substances to the blood circulation system or the central nervous system, when applied at the ear, in the ear or inside of the auditory canal. It is usually preferred, that e.g. the topical excipient does not exhibit any significant excluding properties that would enhance a percutaneous transfer over the mucosa in the systemic circulatory system. Such excipients contain hydrocarbon acids, water-free absorption agents such as hydrophilic petrolatum (Vaseline) and water-free lanolin (e.g. Aquaphor) and substances based on water-oil emulsions such as lanolin and Cold Cream. More preferred are excipients that are substantially none-excluding, usually comprising all those excipients that are water-soluble as well as substances on basis of oil-in-water emulsions (crèmes or hydrophilic ointments) and substances on a water-soluble basis such as polyethylene glycol based excipients and aqueous solutions gelled with various substances such as methyl cellulose, hydroxyethylcellulose and hydroxypropylmethylcellulose.

For oral administration in the form of tablets or capsules, the inventive β-carbolines may be combined with any non-toxic pharmaceutically acceptable adjuvant selected from the list comprising binders, such as corn starch, polyvinylpyrrolidone or hydroxypropylmethylcellulose; fillers such as lactose, saccharose, glucose, mannitol, sorbitol and other reducing and non-reducing sugars, microcrystalline cellulose, calcium sulfate or calcium hydrogen phosphate; lubricants such as magnesium stearate, talcum or silica, stearic acid, sodium stearyl sulfate, glyceryl behanate, calcium stearate and similar; disintegrants such as potato starch or sodium glycolate-starch; humectants such as sodium dodecyl sulfate; coloring agents; flavorings; gelatin; sweeteners; natural and synthetic rubbers such as gum Arabic, tragacanth or alginate; buffer salts; carboxymethylcellulose; polyethylenglycol; waxes and the like.

The tablets can be coated with a concentrated sugar solution, comprising e.g. gum Arabic, gelatine, talcum, titan dioxide, and the like. In another embodiment the tablets can be coated with a polymer, which is soluble in a light volatile organic solvent or a mixture of organic solvents. In preferred embodiments the inventive β-carbolines are formulated as tablets for immediate release or as tablets for extended release. Dosage forms for immediate release allow the release of a majority of the total amount of β-carbolines within a relative short time span of 60 minutes or less and enable quick absorption of β-carbolines. Extended release formulations for oral dosage forms enable a retarded release over longer periods of time thereby reaching a therapeutically effective plasma level of β-carbolines and/or holding this therapeutic effective plasma level stable over a longer period and/or modifying other pharmacokinetic characteristics of β-carbolines.

The inventive β-carbolines can be formulated as soft gelatine capsules by mixing them e.g. with a vegetable oil or polyethylene glycol. Hard gelatine capsules can contain the β-carbolines in granular form by using either one of the above mentioned adjuvants for tablets such as lactose, saccharose, mannitol, starch such as potato starch, corn starch or amylopectine, cellulose derivatives or gelatine. Liquid and semi-liquid forms of the inventive β-carbolines can also be filled into hard gelatine capsules.

The inventive β-carbolines can also be introduced into microcapsules or microbeads that are made of e.g. polyglycolic acid/lactic acid (PGLA). A controlled release of the inventive β-carbolines out of the pharmaceutical composition can be achieved by making use of biocompatible polymers selected from the list comprising polylactic acid, polyglycolic acid, copolymers of polylactic acid and polyglycolic acid, poly-ε-caprolactone, polyhydroxy butyric acid, polyoethoester, polyacetale, polyhydropurane, polycyanoacrylate and cross-linked or amphipathic block copolymers of hydrogels.

In another embodiment of the invention the β-carbolines are provided as an oral liquid formulation. Liquid preparations for oral administration can be provided in form of solutions, syrup, emulsions or suspensions. Alternatively, the oral liquid formulations can be prepared before use by reconstitution of the dry oral formulation with water or another suitable excipient. Preparations for oral administration can be properly formulated such that a controlled or retarded release of the inventive β-carbolines and possibly of other active substance is attained.

If oral administration in liquid form is intended, the inventive β-carbolines can be mixed with non-toxic pharmaceutically acceptable inert excipients such as ethanol, glycerine, water; suspension agents such as sorbitolsyrup, cellulose derivates or edible hydrogenated fats; emulgators such as lecithin or gum Arabic; non-aqueous excipients such as almond oil, oily esters, ethanol or fractionised vegetable oils; preservatives such as methyl- or propyl-p-hydroxybenzoate or sorbic acid; and the like. Stabilisators, e.g. like antioxidants such as butylhydroxyanisole, butylhydroxytoluol, propyl gallate, sodium ascorbate, citric acid can be used to stabilise the dosage forms. For example, the solutions can contain approximately 0.2 weight percent up to approximately 20 weight percent of β-carbolines, wherein the levelling compound is sugar and a mixture of ethanol, water, glycerine and propylene glycol. Optionally, these liquid formulations can contain colorants, flavourings, saccharin, and carboxyl cellulose as thickeners and/or other adjuvants.

In another embodiment, a therapeutically effective dose of the inventive β-carbolines is administered orally in a solution, wherein the solution contains preservatives, sweetener, solubilisers and a solvent. The solution for oral administration can contain one or more buffers, flavourings or further excipients. In yet another embodiment, peppermint or other flavouring is added to the solution of the inventive β-carbolines for oral administration.

For administration by inhalation the inventive β-carbolines can be administered in suitable ways in pharmaceutical form, such as an aerosol spray in a pressurized container or a nebulizer with a suitable propellant such as dichlorofluoromethane, trichlorofluoromethane, dichlorotetrafluoroethane, carbon dioxide or another suitable gas. When a pressurized aerosol is used, the dose can be determined by providing a valve to administer a measured quantity. Capsules and cartridges made of e.g. gelatine for use in inhalators or insufflators can be formulated such that the capsules and cartridges contain a powder mixture of the inventive β-carbolines and possibly one or more active substances and a suitable powder basis substance such as lactose or starch.

Solutions for parenteral administration by injection can be prepared in an aqueous solution of a water-soluble pharmaceutically acceptable salt of the inventive β-carbolines in a concentration of approximately 0.5 weight percent up to approximately 10 weight percent. These solutions can further contain stabilizers and/or buffer substances and can be provided in appropriate manners in ampoules with different doses units.

Hence, all compounds presented here are useful for the manufacture of pharmaceutical formulations for prophylaxis and/or prevention of acute and chronic ear disorders and hearing damages, vertigo and vestibular disorders, in particular acute hearing loss, acute acoustic trauma, labyrinthine deafness due to chronic noise exposure, presbycusia, trauma during implantation of inner ear prosthesis (insertion trauma), vertigo due to diseases of the inner ear, vertigo in relation with and/or as a symptom of Menière's disease, vestibular disorders in relation with and/or as symptom of Menière's disease, tinnitus and hearing damages due to antibiotics and cytostatics.

FIGURE DESCRIPTION

FIG. 1 shows a graphic account of quantitative RT-PCR (real-time PCR) of inner ear cells (organ of Corti of the cochlea) of rat after exposition to 90 μM 9-methyl-β-carboline (9-Me-BC) for 48 hours or solvent (100%), respectively. Values above 100% mean that 9-Me-BC activated transcription of the corresponding gene in the course of incubation while the opposite is valid for values under 100%.

Figure 2:
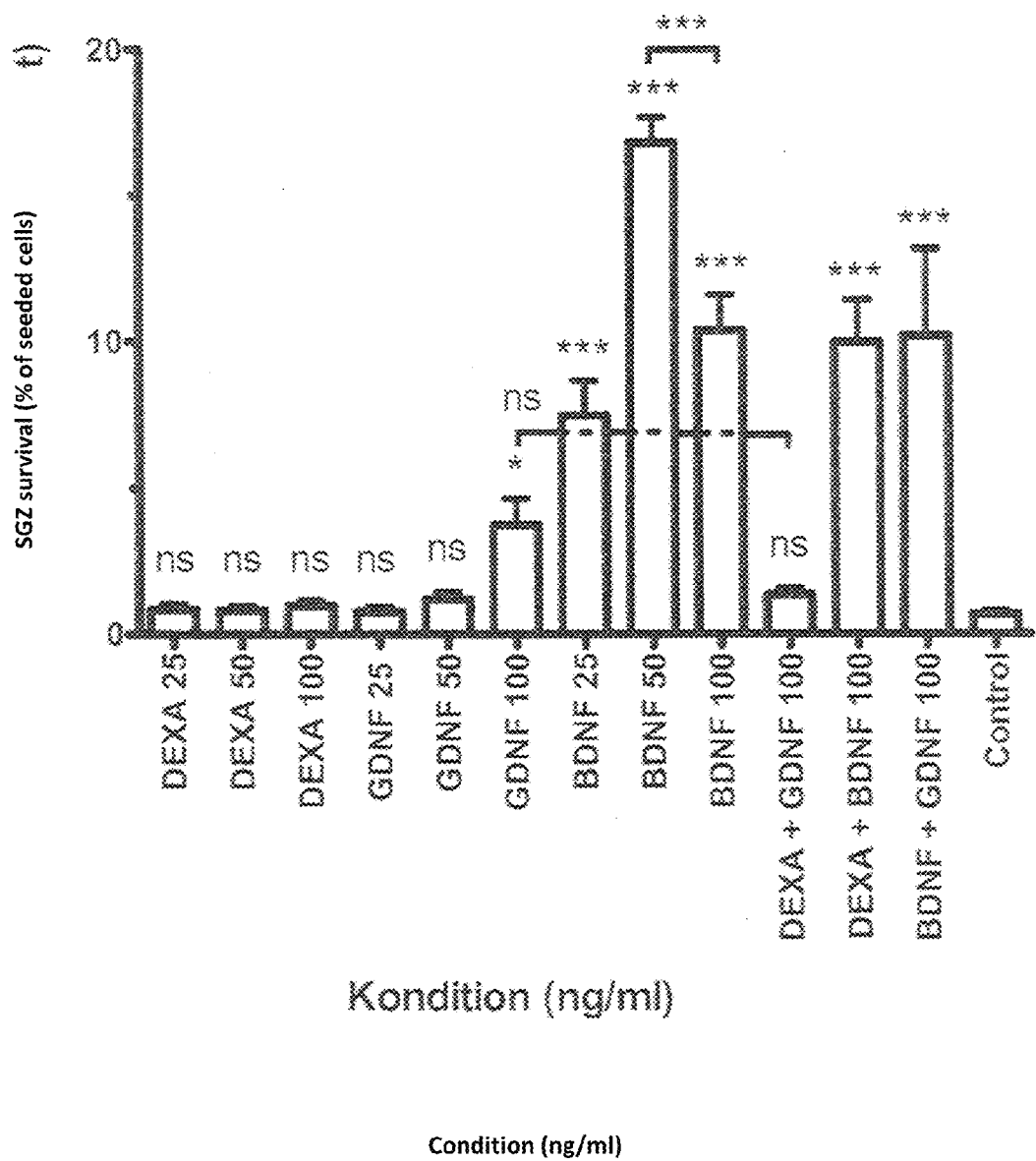

Abbreviations used in FIG. 1 have the following meaning:
   Armetl1: conserved dopamine neurotrophic factor
   BDNF: brain-derived neurotrophic factor
   BMP2: bone morphogenetic protein 2
   Cbln1: cerebellin 1 precursor protein
   DAT: dopamine transporter
   DEXA: dexamethasone
   DRD1: dopamine receptor subtype 1
   DRD2l: long variant of the dopamine receptor subtype 2
   GDNF: Glial cell line derived neurotrophic factor
   NGF: nerve growth factor
   NPY: neuropeptide Y
   Nurr 1: nuclear receptor regulated 1 protein
   PTX: paired-like homeodomain transcription factor
   Ret: rearranged during transfection receptor
   RKIP: raf-1 kinase inhibitor protein
   Sirt: silent information regulator
   Th: tyrosine hydroxylase
   TNF: tumour necrosis factor FIG. 2 shows a graphic account of the effects of different concentrations and combinations of Glial cell line derived neurotrophic factor (GDNF), brain-derived neurotrophic factor (BDNF) and dexamethasone (DEXA) on the survival of cells of the spiral ganglion of the inner ear after 48 hours of culture. Column height reflects mean±standard errors and represents 24-32 observations of three or four different experiments. Significances of the different comparisons to the control group are shown over the bars whereas other comparisons are depicted separately by parentheses (P<0.05 *; P<0.01 ; P<0.001 *). Source: *Jahresbericht Medizinische Hochschule Hannover* 2005, Department of Ear, Nose and Throat Diseases (director: Th. Lenarz).

Figure 3A:
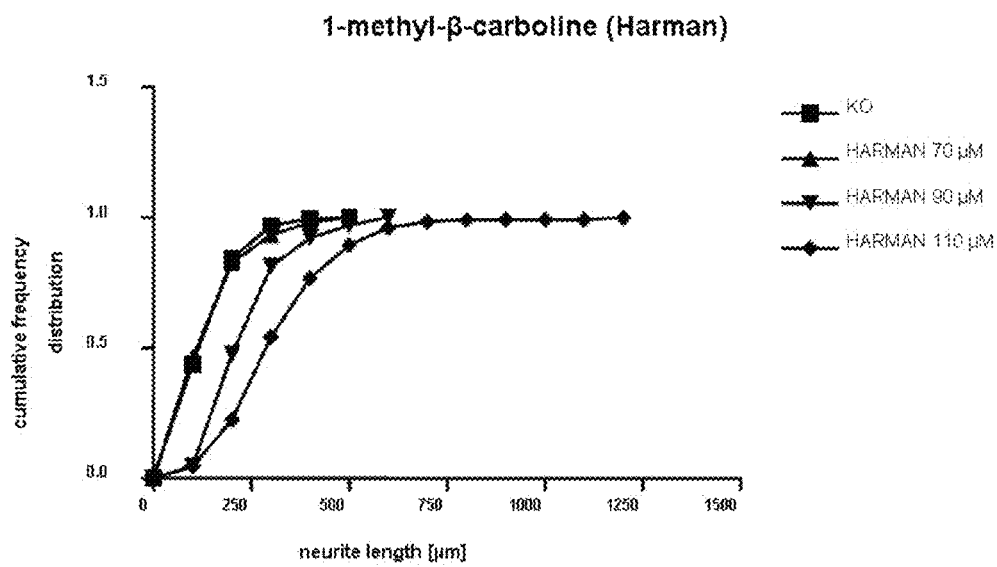

FIG. 3A shows the neurite length of humane SH-SY5Y cells treated with Harman for 14 days in culture, as described above. The difference between the control group and the group treated with 110 μM Harman was significant (P<0.001). Thus, Harman treatment led to an increase in neurite length.

Figure 3B:
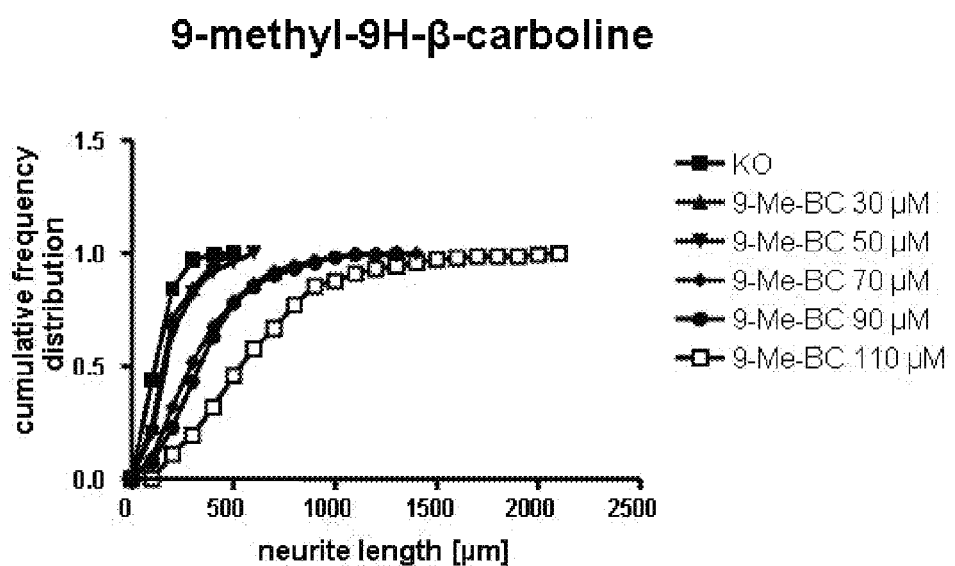

FIG. 3B shows the neurite length of human SH-SY5Y cells treated with 9-methyl-9H-β-carboline for 14 days, as described above. The difference between the control group and the groups treated with 70, 90 or 110 μM 9-methyl-9H-β-carboline, was significant (P<0.001). Thus, 9-methyl-9H-β-carboline treatment led to an increase in neurite length.

Figure 3C:
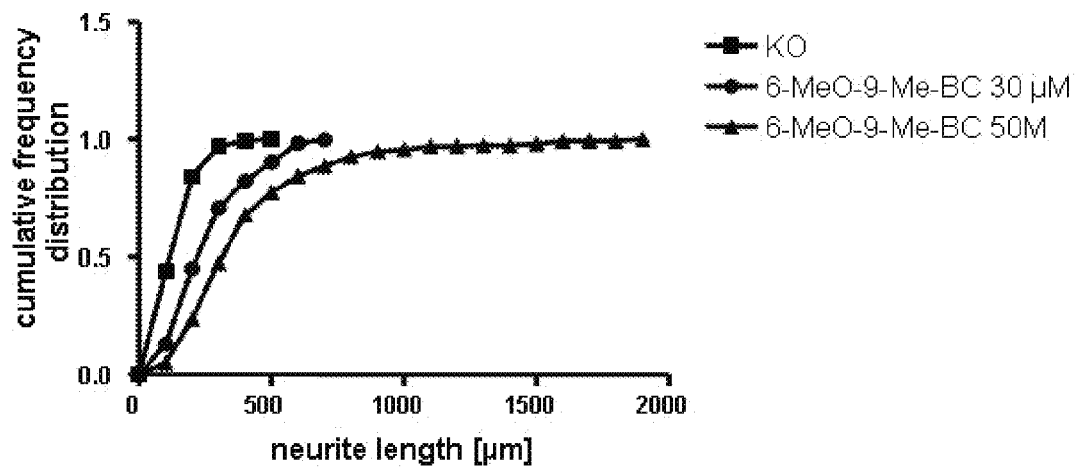

FIG. 3C shows the neurite length of human SH-SY5Y cells treated with 6-methoxy-9-methyl-9H-β-carboline, as described above. The difference between the control group and the group treated with 50 μM 6-methoxy-9-methyl-9H-β-carboline, was significant (P<0.001). Thus, 6-methoxy-9-methyl-9H-β-carboline treatment led to an increase in neurite length.

Figure 3D:
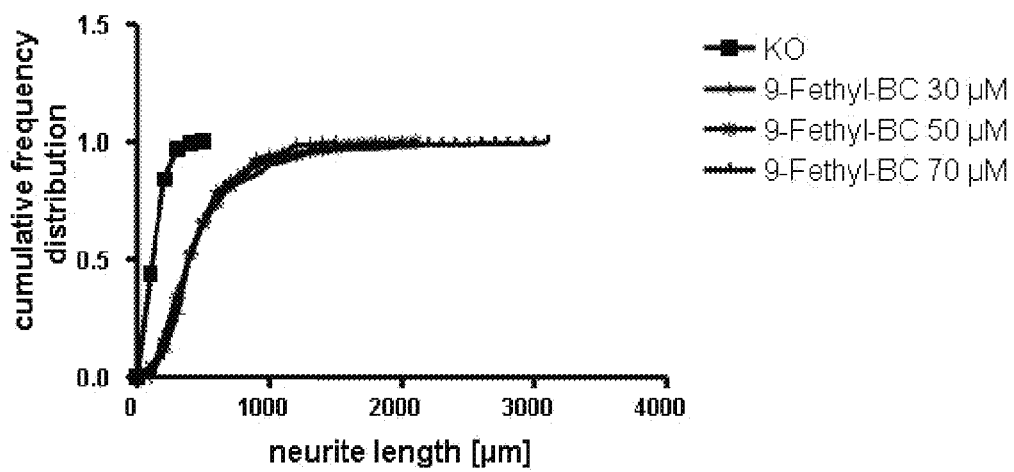

FIG. 3D shows the neurite length of human SH-SY5Y cells treated with 9-(2-fluoroethyl)-9H-β-carboline, as described above. The difference between the control group and the groups treated with 30, 50 or 70 μM 9-(2-fluoroethyl)-9H-β-carboline, was significant (P<0.001). Thus, 9-(2-fluoroethyl)-9H-β-carboline treatment led to an increase in neurite length.

Figure 4A:
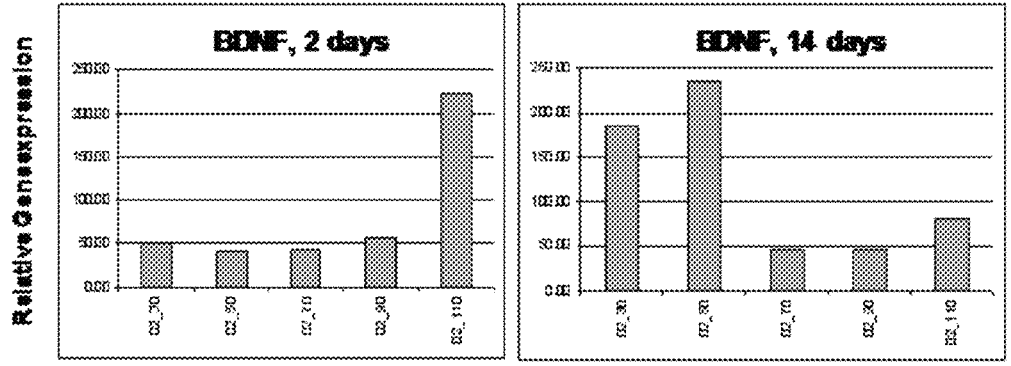
Figure 4A:
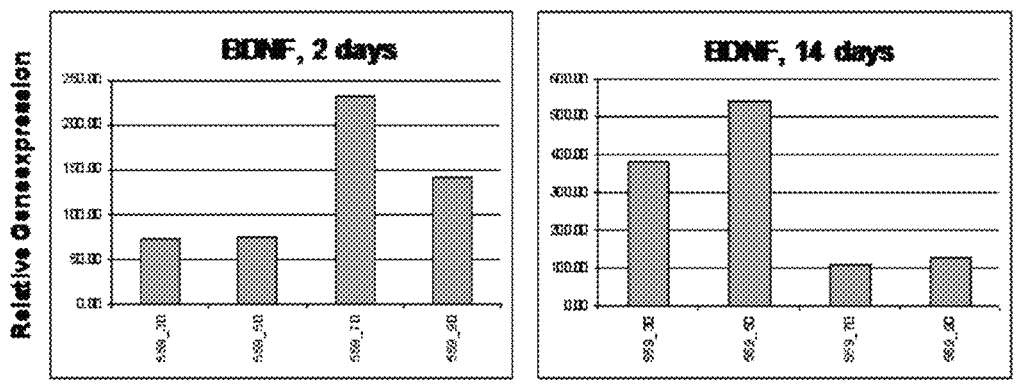
Figure 4A:
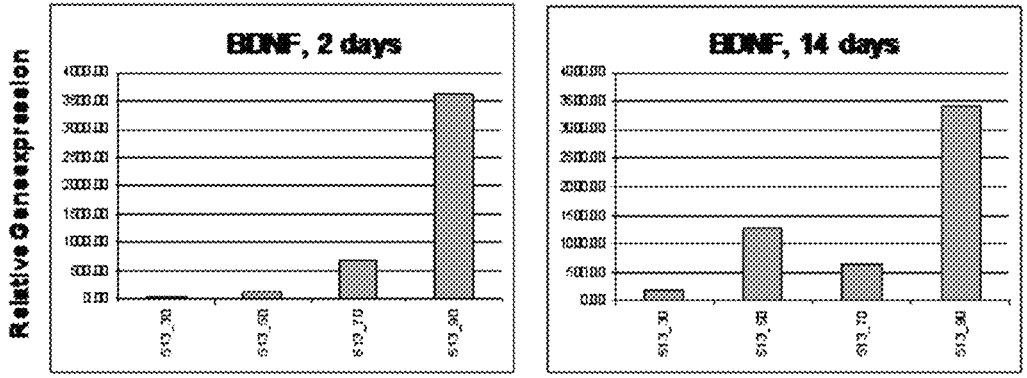

FIG. 4A shows the relative gene expression of BDNF (brain-derived neurotrophic factor) in human SH-SY5Y cells. The transcription of BNDF after two days was stimulated only at the highest concentration (110 μM) of LE-02 (9-methyl-β-carboline), whereas after 14 days of exposition the lower concentrations of 30 and 50 μM induced stimulation. Such a shift was also found for 9-fluoroethyl-β-carboline (substance no. 559 in FIG. 4A; after two days: stimulation by 70 and 90 μM; after 14 days by 30 and 50 μM). In contrast, 6-methoxy-9-methyl-9H-β-carboline (substance no. 513 in FIG. 4A) led to an enormous, dose-dependent increase of BDNF transcription.

Figure 4B:
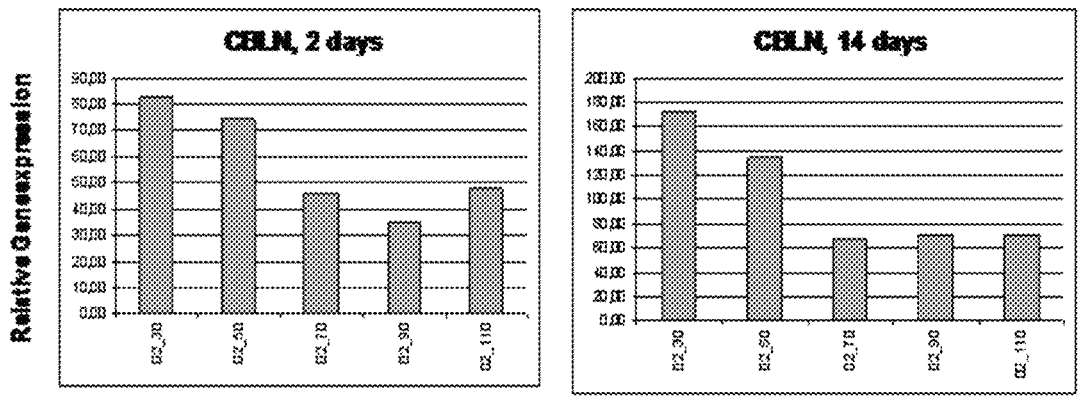
Figure 4B:
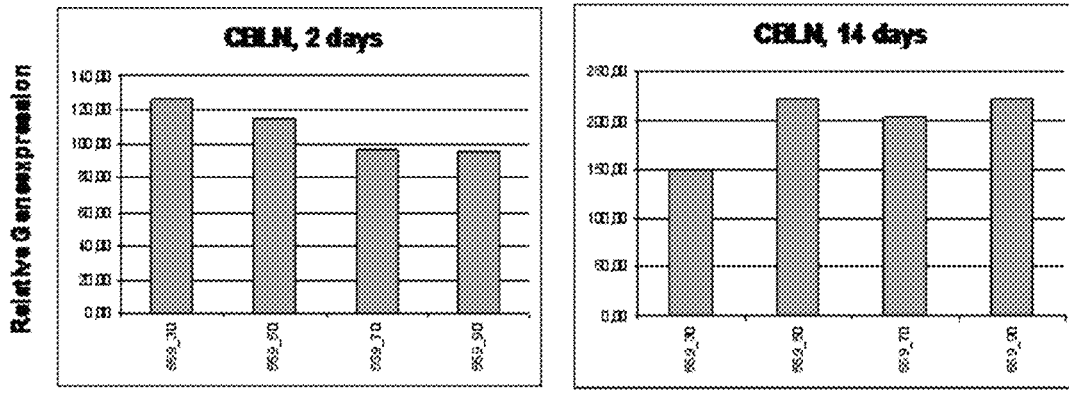
Figure 4B:
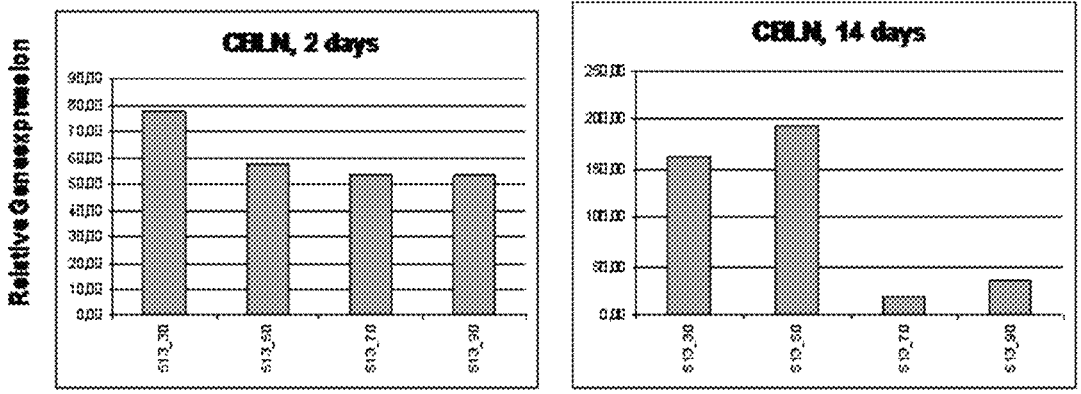

FIG. 4B shows the relative gene expression of cerebellin-1 precursor protein (CBLN). Cerebellin-1 precursor protein was increased only after two days exposure to 9-fluoroethyl-β-carboline. After 14 days of exposure, all tested 6-carbolines increased CBLN expression. Lower concentrations of the test substances had a stronger effect than higher concentrations with the exception of 9-fluoroethyl-β-carboline, showing roughly the same stimulation at all investigated concentrations.

Figure 4C:
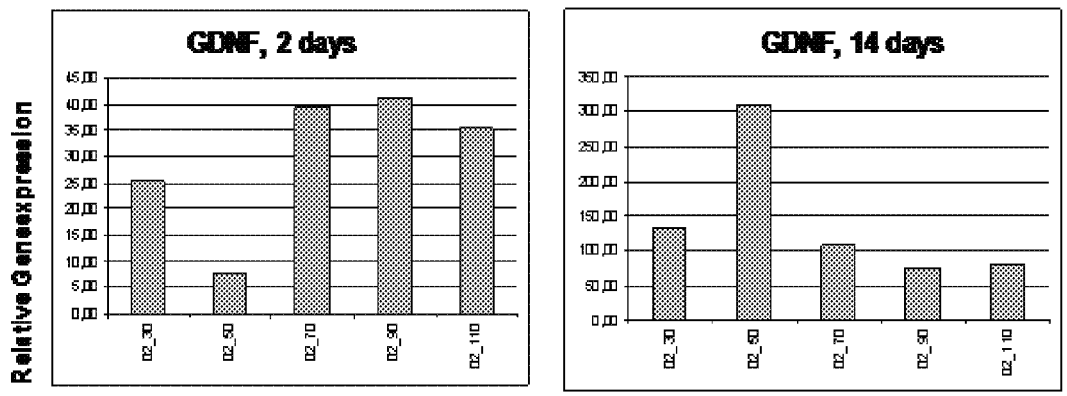
Figure 4C:
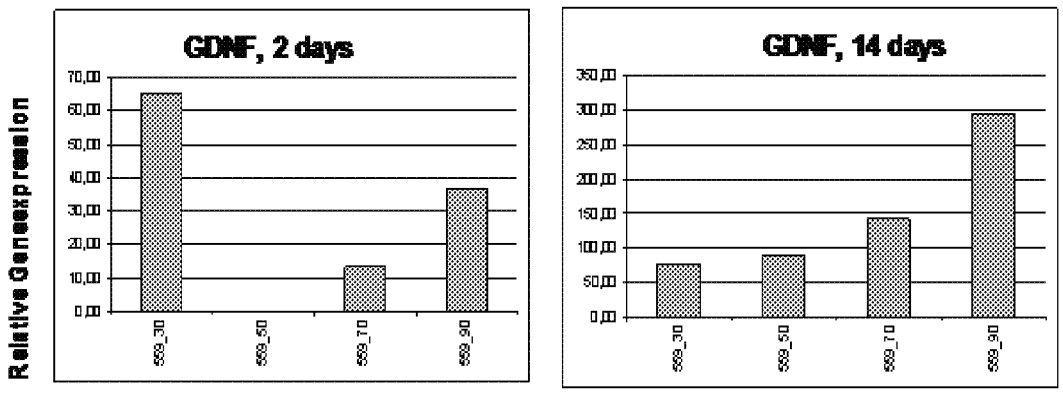
Figure 4C:
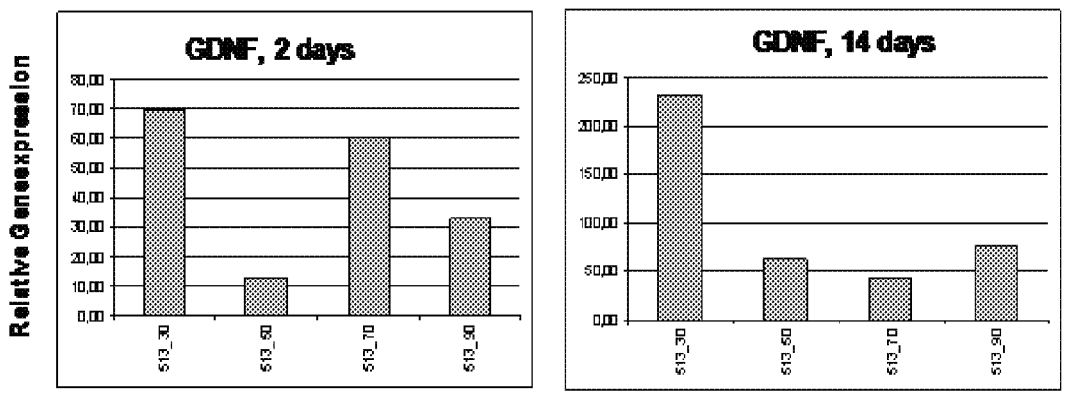

FIG. 4C shows the relative gene expression of GDNF (glial cell line-derived neurothrophic factor). At individual concentrations, 14 days of exposure led to a stimulation of up to three times.

Figure 4D:
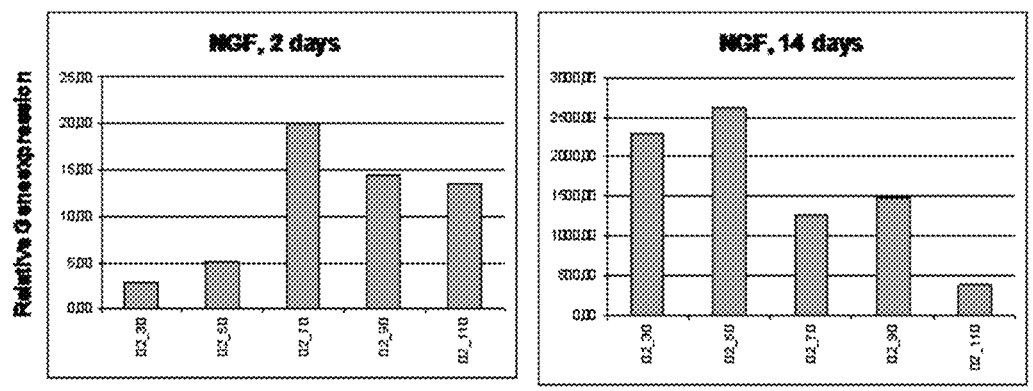
Figure 4D:
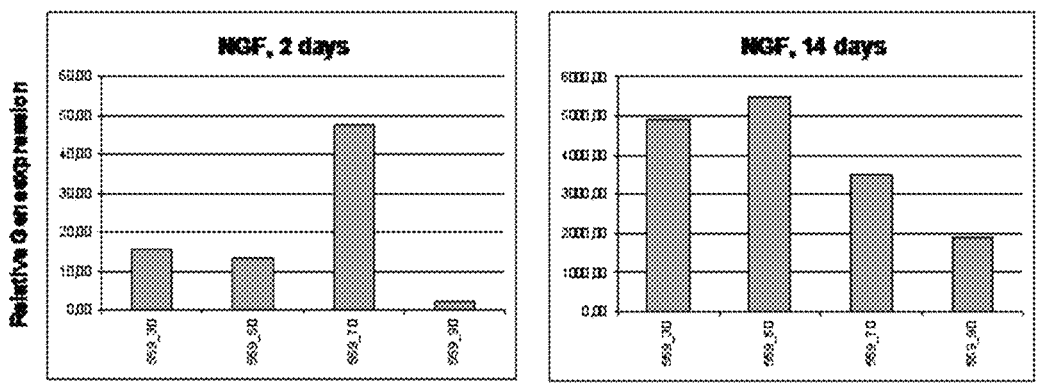
Figure 4D:
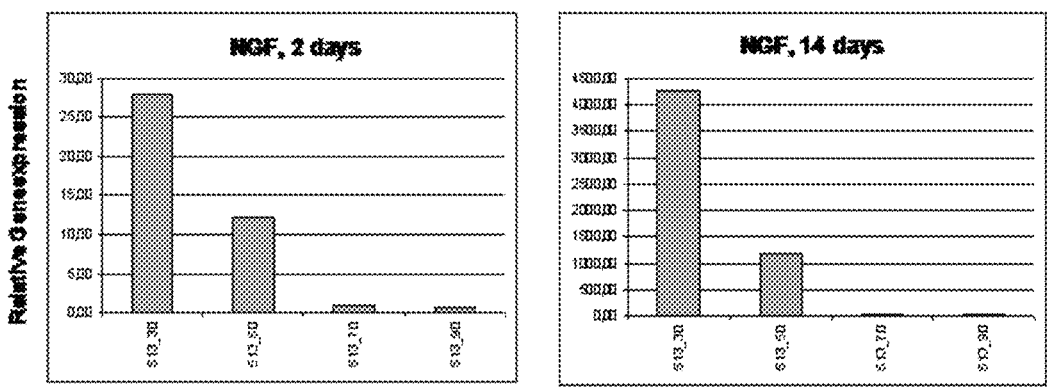

FIG. 4D shows the relative gene expression of NGF (nerve growth factor). After 14 days of exposure the gene expression was increased by 20 to 50 times. Again, the lower concentrations were far more effective in increasing NGF.

Figure 4E:
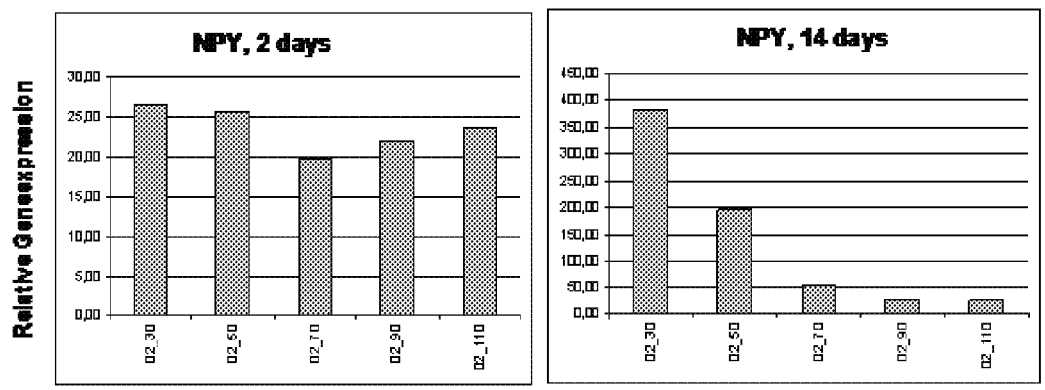
Figure 4E:
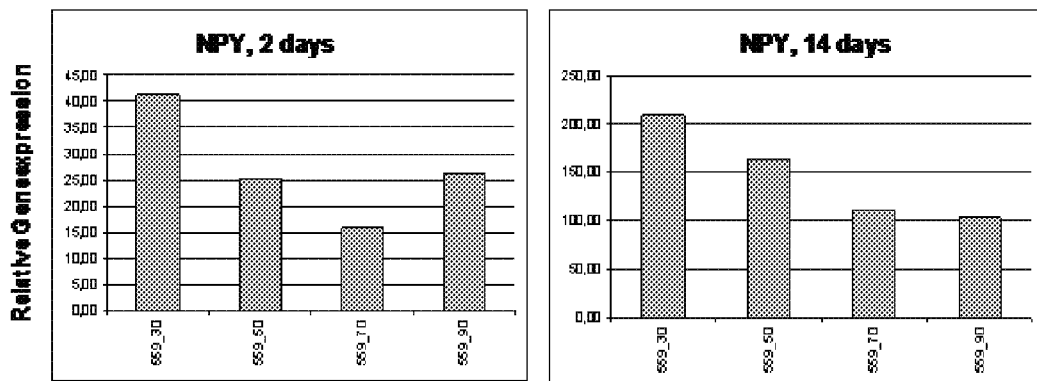
Figure 4E:
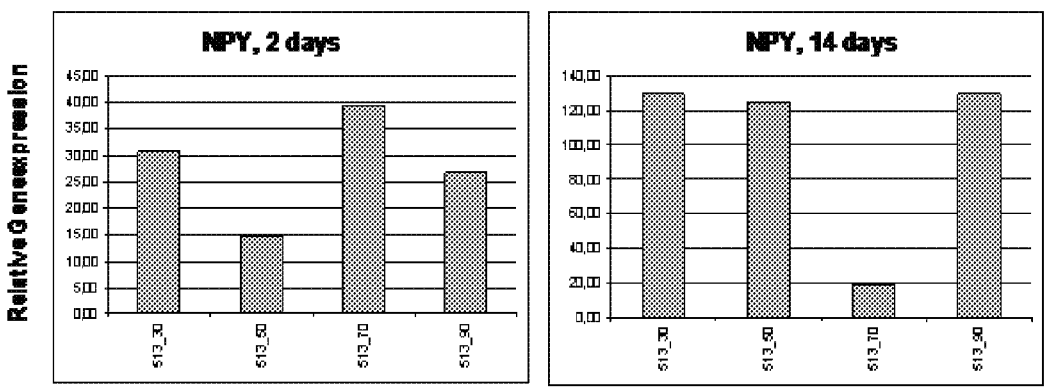

FIG. 4E shows the relative gene expression of NPY (Neuropeptide Y). After 14 days of exposure the gene expression was increased by 1.3 to 4 times. In case of 9-methyl-β-carboline and 9-fluoroethyl-β-carboline the lower concentrations were more effective than the higher concentrations.

Figure 5:
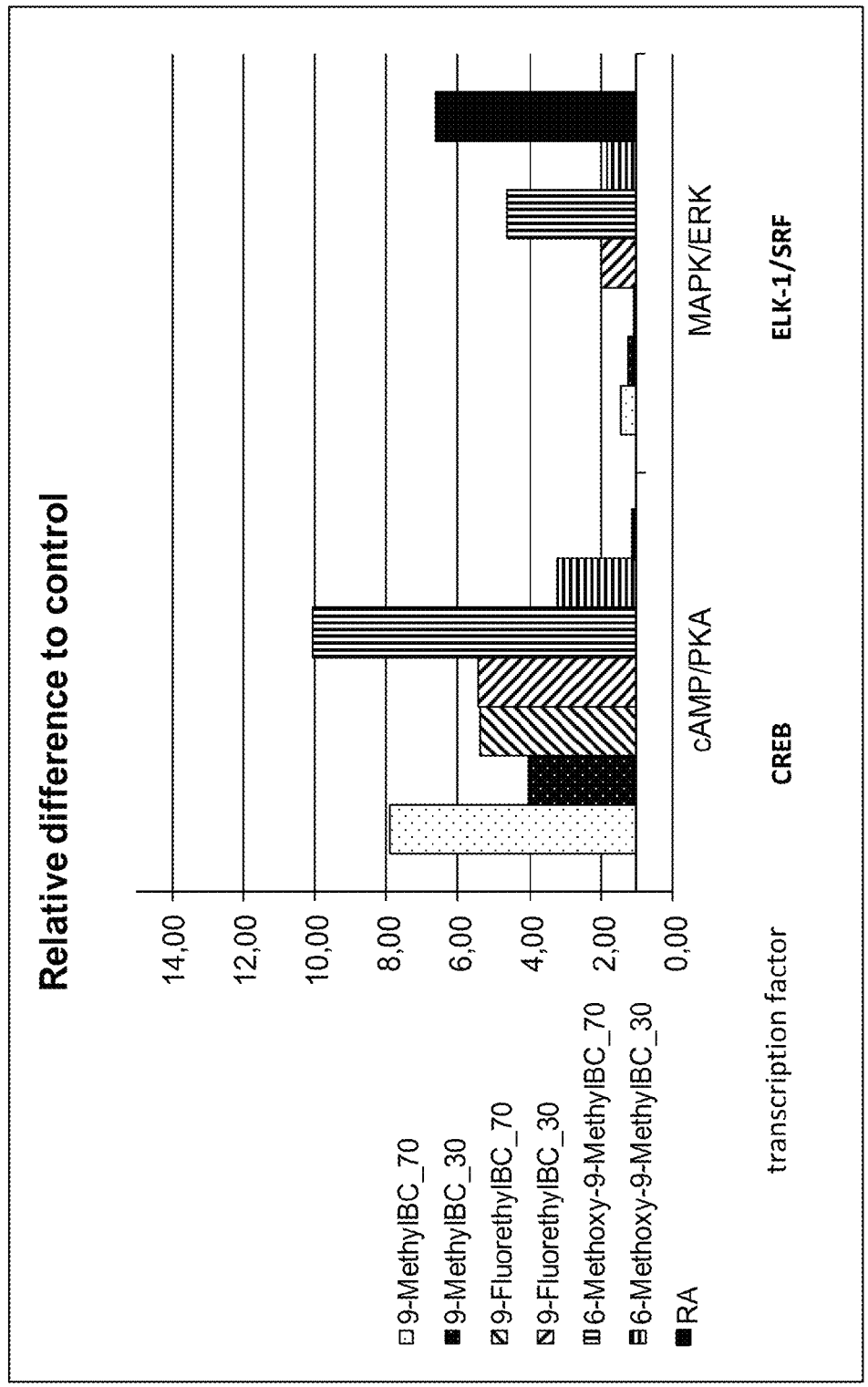

FIG. 5 shows a dose-dependent, activating effect of 9-methyl-β-carboline, 9-fluoroethyl-β-carboline and 6-methoxy-9-methyl-9H-β-carboline on the formation of the transcription factor CREB, up to ten times of the level in the control cells SH-SY5Y (three independent experiments, 48 h incubation).

Figure 6A:
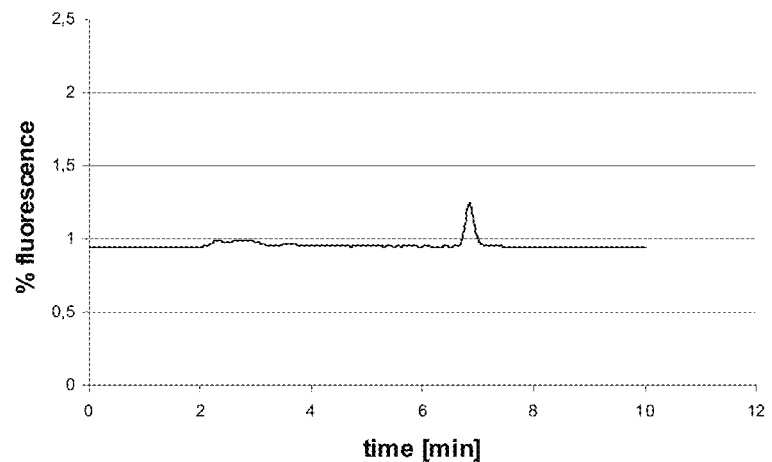
Figure 6B:
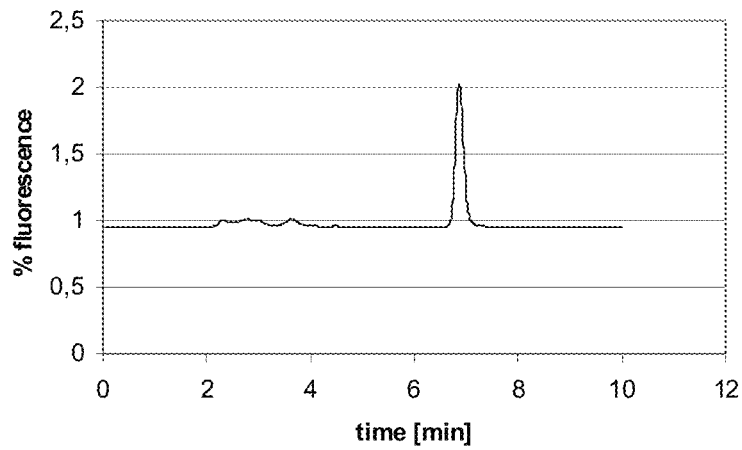
Figure 6C:
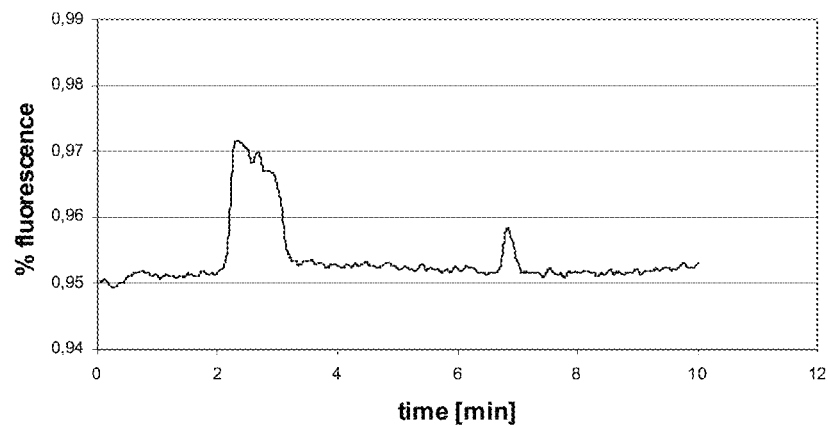
Figure 6D:
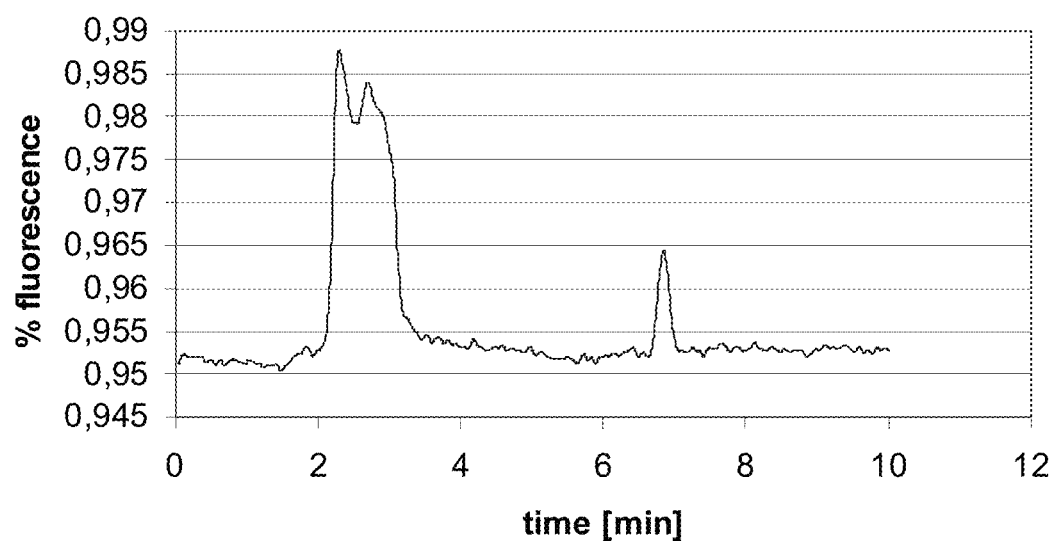
Figure 6E:
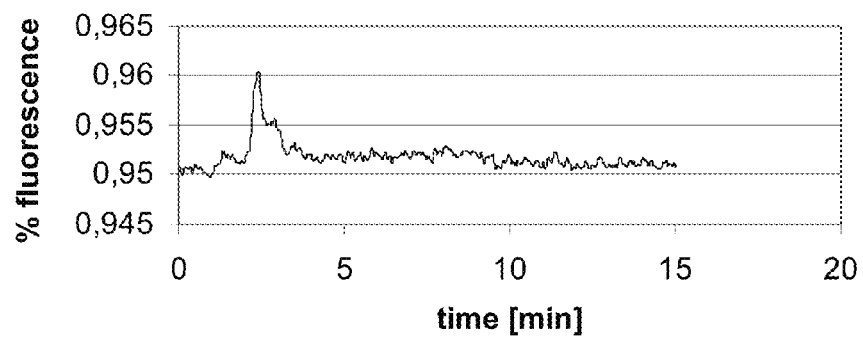
Figure 6F:
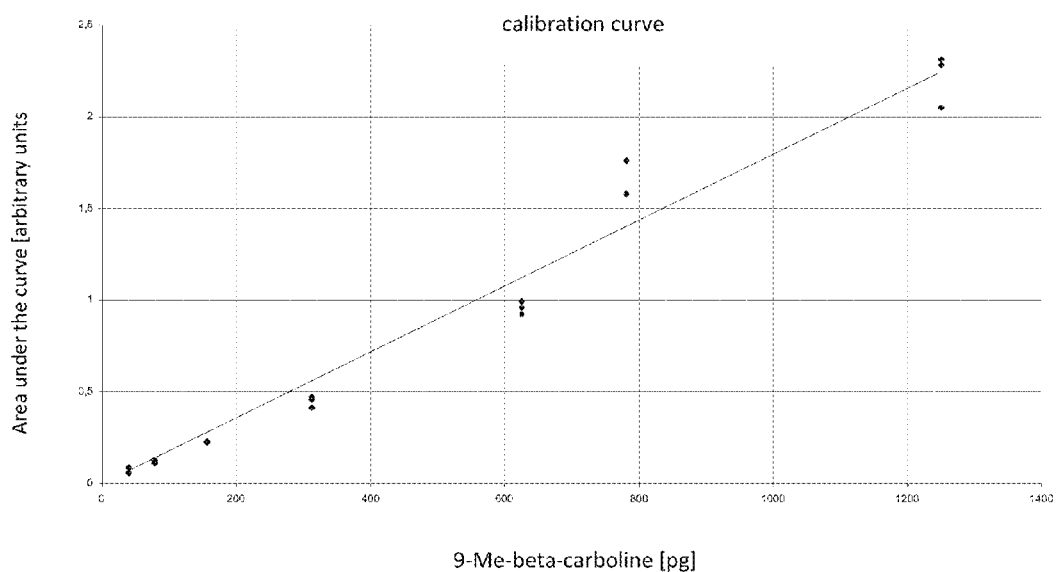

FIG. 6 the FIGS. 6A to 6F show chromatograms of perilymph, which were obtained by the experiments of example 29. Chromatograms according to the FIGS. 6A and 6B were recorded for perilymph, which had been obtained after a three-hour (FIG. 6A) or ten-hour injection (FIG. 6B) of 9-Me-BC into the inner ear region of guinea pigs for three hours. Chromatograms according to the FIGS. 6C and 6D were recorded for perilymph, which had been obtained after a three-hour or twenty-hour straight injection of 9-Me-BC into the cochlea of guinea pigs. The chromatogram according to FIG. 6E was recorded for perilymph, which had been exposed to no treatment with 9-Me-BC. The chromatogram according to FIG. 6F depicts a straight calibration line, wherein the concentration of 9-Me-BC was assigned to an area under the chromatographic maximum obtained for it.

EXAMPLES

Example 1

Synthesis of 9-methyl-β-carboline

A stirred solution of 13 g (0.0756 Mol) 1,2,3,4-tetrahydro-β-carboline, manufactured by tryptamine hydrochloride and glyoxylic acid as described by Ho and Walker (1988), and 2.6 g Pd/C (10%) in 600 ml of cumene were refluxed in a nitrogen atmosphere for 90 min. After addition of 100 ml of ethanol, the hot solution was filtrated, and the coal was extracted thrice by 30 ml of hot ethanol. The combined liquid fractions were concentrated, and the residues was crystallised in toluene to yield 10.5 g (82%) or norharman. Methylation at position 9 was performed as described in the literature (Ho B T, Mcisaac W M, Walker K E, Estevez V, J Pharm Sci 57: 269, 1968) yet with an improved reprocessing. One gram (5.95 mmol) of norharman was dissolved in 10 ml of dried DMF in a nitrogen atmosphere. After that, 0.36 g (14.9 mmol) of sodium hydride were added in form of a 60% dispersion in paraffin at 0° C. After cooling of the reaction mixture down to room temperature, this was cooled down to −10° C., and 0.84 g (5.95 mmol) iodomethane were added. After further stirring for 12 hours, one allowed the mixture to cool down to room temperature once again. All volatile ingredients were removed in reduced pressure. After that, 100 ml of water were added, and the mixture was extracted by 3×50 ml of CHCl$_3$. The combined organic fractions were washed with 5×20 ml of water and were evaporated for drying. The residue was suspended in 100 ml 2 N hydrochloric acid. To separate the educt from the desired methylated product, ion pair exchange extraction of the HCl salt was performed in CHCl$_3$ by a liquid/liquid extractor for two days. After removal of the solvent one yielded 0.7 g (64%) of yellow crystals of 9-methyl-β-carbolinium hydrochloride.

Melting point: 295° C.; GC/MS of the free base: m/z=182 (100%), 167 (5%), 140 (10%), 127 (10%), 113 (5%), 91 (10%). $^1$H-NMR(HCl salt): δ (ppm) methanol d4, 250 MHz: 4.06 s, 3H, N—CH$_3$; 7.28-7.35, dt, J=1.2; 6.8, 1H, H6; 7.58-7.70, m, 2H, H7, H8; 8.13-8.16, d, J=5.4, 1H, H4; 8.18-8.21, d, J=7.9, 1H H5; 8.31-8.33, d, J=5.4, 1H, H3; 8.89, s, 1H, H1.

Examples 2-13

Production of the Compounds A to L

Synthesis of the compounds A to L is carried out according to example 1 in that the corresponding alkyl iodides, alkyl

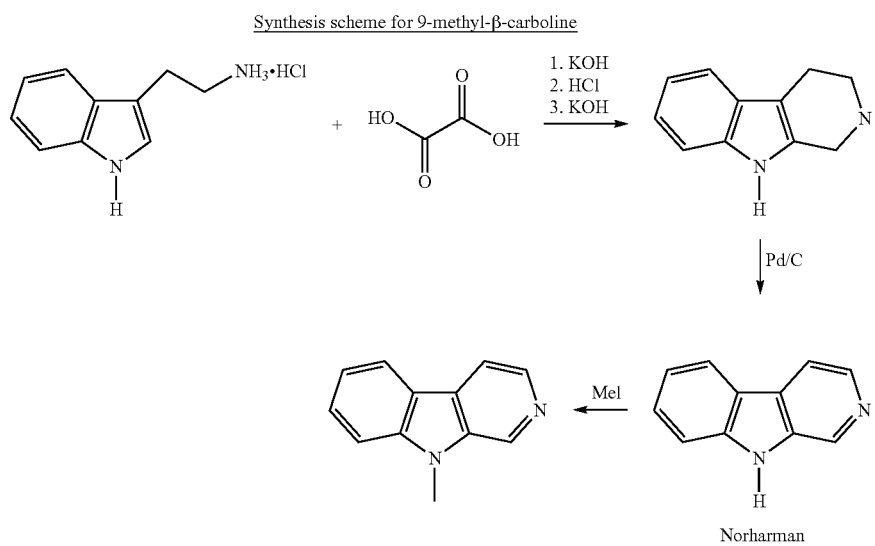

Synthesis scheme for 9-methyl-β-carboline bromides or alkyl tosylates were used. Yields were between 30 and 75% of the theoretical yield.

Example 14

Studies of Inner Ear Cells (Cochlea) of Rat

Experiments were conducted for the proof of effectiveness of the β-carbolines according to invention in order to determine, which effects this class of compounds will have on ear diseases, hearing damages and vertigo. 9-Methyl-β-carboline (9-Me-BC, VI) was selected as an example compound. The effectiveness of the other tested substances will be put in relation to the effectiveness of 9-methyl-β-carboline (9-Me-BC, VI).

Initially, organ cultures of the organ of Corti of the cochlea of rats were prepared, which were brought into contact with 9-methyl-β-carboline in a next step. Expression of different neurotrophins was measured as a marker of the effects of 9-methyl-β-carboline on the organs or Corti. For this, RNA was isolated from Corti's tissue, transcribed into cDNA, and the concentrations of the cDNAs of the neurotrophins were determined with help of the real-time RT-PCR method.

Organs of Corti of the cochlea of 40 rats were prepared in several sessions on day 4 post partum. Then, the organ culture was exposed either to 9-Me-BC at a concentration of 90 µM for 48 hours or to a corresponding amount of solvent (control conditions). After that, the organ culture was washed with PBS-EDTA (PBS-EDTA of BioChrom, diluted 1:27 by PBS). Then the sample was frozen at −80° C. Total RNA was isolated using the RNEasy Lipid Tissue Mini Kit of Qiagen, Hilden. DNAse digestion was carried out with the sample of isolated RNA with subsequent several washing steps according to the instructions of the manufacturer of the kit. RNA was eluted by RNase-free water. Amount and quality of the RNA were determined photometrical. One microgram of RNA of each sample was transcribed into complementary DNA (cDNA) using a kit of Roche Applied Science, Mannheim. Real-time reverse transcriptase polymerase chain reaction (real-time RT-PCR) was performed with the LightCycler System of Roche Applied Science, Mannheim, using the fluorescence resonance energy transfer (FRET) method. For this, the LightCycler FastStart DNA Master Hybridisation Probes Kit of the same company was used. The gen for hydroxymethylbilane synthase (HMBS) was selected as a so-called housekeeping gene for relative quantification. Suitable primers and probes were designed and synthesized by TIB Molbiol, Berlin. Twenty-five micrograms of cDNA were added to each reaction. Cycling conditions were as following: denaturation at 94° C. for 5 min, 55 cycles of 7 sec with denaturing conditions, binding of primers and probe at the suited temperature for 10 sec and elongation at 72° C. for 10 sec. Then, melting point curve analysis was conducted. The measured fluorescence of each cycle was analysed by the LightCycler Software. The relative amount of target of each sample resulted from the comparison to the amount of the housekeeping gene of the same sample. Quantification was conducted by the $2^{-\Delta\Delta C(t)}$ method of Livak and Schmittgen (Livak K J and Schmittgen T D. *Analysis of relative gene expression data using real-time quantitative PCR and the 2(-Delta Delta C(T)) Methods* 2001; 25:402-8).

The amounts of RNA obtained in each single round were very small in comparison to those typically obtained from brain regions. Therefore, targets had to be selected carefully based on the state of scientific findings. It resulted from this: first, a medicament should stop or even reverse the degeneration of nerve cells in general, which, in deed, are damaged in all diseases of the inner ear, because a single cause for the differences in the diseases of the inner ear can be excluded. According to the state of the art, only neurotrophins (growth factors of nerve cells) come into consideration. Neurotrophins are endogenous peptides, which play an important role in generation, differentiation, and viability of nerve cells. For this, the individual types of nerve cells are particularly dependent on the presence of specific neurotrophins. The second scientific finding is as below: Deafness is based on a disorder of nerve cells of the dopaminergic nerve types in particular. Therefore, a medicament preferably should activate dopaminergic mechanisms.

As shown in FIG. 1, generation of several neurotrophins was activated, of whose is known that they possess neuroprotective properties in general. These are Armetl 1, BDNF, Cbln 1, NGF and NPY (for an explanation of the abbreviations see legend to FIG. 1). Moreover, dopaminergic proteins were increasingly activated such as the dopamine receptor subtype 1 and tyrosine hydroxylase, which synthesises dopamine in nerve cells. It is known that the dopamine receptor 1 is the subtype, which is the type to be found most in the inner ear by far. Several independent experiments of almost identical results were conducted (standard deviation <10%). Therefore, results were reproducible very well.

Theses results prove that 9-Me-BC activates specifically characteristic proteins of dopaminergic nerve cells. No substance has been described so far, which has such a spectrum of effects. This is exceptionally advantageous insofar as the effects in detail counteract precisely the processes, which play an eminent role in labyrinthine deafness according to current knowledge. Thus, 9-Me-BC is a compound with a unique mode of effectiveness that particularly is suitable for stopping or even reversing degenerative processes of nerve cells, in particular of dopaminergic nerve types.

Th. Lenarz and his co-workers of the *Medizinische Hochschule Hannover*, who run the largest cochlear implant centre worldwide, prepared the research presented in FIG. 2 in 2005. They exposed the spiral ganglion, i.e. a part of the acoustic nerve, to different substances for 48 hours to test, which of them will have neuroprotective properties. As shown by FIG. 2, these particularly are BDNF and GDNF. Conclusion of this study was that substances that activate BDNF and GDNF are promising therapeutics against damages of the inner ear. At that time, i.e. 2005, such substances were unknown. These results of a different group with worldwide recognition delineate, therefore, the therapeutic potential of 9-methyl-BC. It is to be noted that, as large peptides, neither BDNF nor GDNF themselves are suited to be applied locally. In contrast, 9-methyl-BC is a relatively small substance (MW: 183), which is lipophilic and chemically stable and is metabolised slowly only, if at all (see example 29).

Examples 15-28

Differentiation Model of Human Neuroblastoma Cells (SH-SY5Y)

The previous examples were conducted in animal models with rats and guinea pigs, thus for the following examples it was an essential aspect, to prove, whether β-carbolines would also act in human tissue pro-differentiating through induction of growth factors. Therefore, several experiments were conducted with human SH-SY5Y neuroblastoma cells.

Organs of Corti of more than 40 rats had to be prepared and analysed to obtain reproducible and reliable information about the spectrum of effectiveness of 9-ME-BC. This is an enormous labour input and number of animals. Therefore, compounds XI, XII, XVIII, XIX as well as C to L were analysed in the differentiation model as described below. Since no cell lines or differentiation models for hair cells of the middle ear exist, other cell lines, such as neuroblastoma cell lines had to be utilized, which show similar differentiation characteristics as the hair cells of the middle ear.

Human neuroblastoma cells were utilised for this model. These are permanent cells, which are present as an indifferent type in culture. They can be activated to differentiate, i.e. transformation into neuronal cells, by addition of specific substances such as retinoic acid, brain-derived nerve growth factor (BDNF) or activator of the enzyme, protein kinase C to the culture medium. We used this cell system to analyse whether beta-carbolines can transform the indifferent cells into the neuronal type. Criteria were: less proliferation (less cells per field of view); smaller cell bodies (transformation from the indifferent type to the neuronal type); cytodendrites (neuritis), which provide connections to neighbouring cells or clusters of neighbouring cells. This resulted in the following results:

TABLE 1

Further β-carbolines in comparison to 9-methyl-β-carboline

| 9-methyl-β-carboline | standard |
|---|---|
| fluorethyl-BC (XIX) | + |
| 9-Me-6-MeO—BC (XVIII) | + |
| compound C | ± |
| compound D | + |
| compound (XI) | + |
| compound (XII) | + |
| compound E | + |
| compound F | ± |
| compound G | ± |
| compound H | + |
| harman | − |
| compound J | ± |
| compound K | ± |
| compound L | + |
| compound (XVI) | − |
| compound (XVII) | ± |
| compound (VII) | − |
| compound B | − |
| compound (XIII) | ± |
| compound (XIV) | − |
| compound A | − |
| compound (XX) | − |
| compound (VIII) | ± |
| compound I | − |
| compound (XV) | ± |
| compound (IX) | − |
| compound (X) | ± |

+: marginally better than 9-methyl-β-carboline
±: equal to 9-methyl-β-carboline
−: marginally worse than 9-methyl-β-carboline As shown by Table 1, the beta-carbolines analysed by us are in deed able to promote differentiation at varying extents.

The FIGS. 3 to 5 complement and illustrate the data as shown in table 1.

Measurements of Neurite Length as Indication for Pro-Differentiation Effects:

Human SH-SY5Y neuroblastoma cells were incubated in culture for 14 days with solvent (Ko) or test substance. A shift of the graph to the right side for a test substance, pointed to an increase of neurite length, when compared to the graph for the control substance. Statistical differences between the treated groups were calculated with the Tukey's Multiple Comparison-Test.

FIG. 3A shows the neurite length of humane SH-SY5Y cells treated with Harman, as described above. The difference between the control group and the group treated with 110 µM Harman was significant (P<0.001). Thus, Harman treatment led to an increase in neurite length.

FIG. 3B shows the neurite length of human SH-SY5Y cells treated with 9-methyl-9H-β-carboline, as described above. The difference between the control group and the groups treated with 70, 90 or 110 µM 9-methyl-9H-β-carboline, was significant (P<0.001). Thus, 9-methyl-9H-β-carboline treatment led to an increase in neurite length.

FIG. 3C shows the neurite length of human SH-SY5Y cells treated with 6-methoxy-9-methyl-9H-β-carboline, as described above. The difference between the control group and the group treated with 50 µM 6-methoxy-9-methyl-9H-β-carboline, was significant (P<0.001). Thus, 6-methoxy-9-methyl-9H-β-carboline treatment led to an increase in neurite length.

FIG. 3D shows the neurite length of human SH-SY5Y cells treated with 9-(2-fluoroethyl)-9H-β-carboline, as described above. The difference between the control group and the groups treated with 30, 50 or 70 µM 9-(2-fluoroethyl)-9H-β-carboline, was significant (P<0.001). Thus, 9-(2-fluoroethyl)-9H-β-carboline treatment led to an increase in neurite length.

Inkubation of human SH-SY5Y neuroblastoma cells for 14 days in culture led to an increase in neurite length. Shown are the cumulative frequency distributions of neurite lengths, determined in at least 20 randomly selected visual fields (each 640.000 µm$^2$) in three independent experiments. A steep rise pointed to a predominance of short neuritis, wherein for example in control cells, a less steep rise signified a greater number of longer neurites. The horizontal maximum indicated the maximal neurite length of the respective treatment group. The results show that the inventive β-carbolines promote the sprouting of neurites. The effects are dose- and substance-dependent: 1-methyl-β-carboline <6-methoxy-9-methyl-β-carboline <9-methyl-β-carboline <9-fluorethyl-β-carboline). Hence, the β-carbolines have a pro-differentiation effect.

The effects of the other inventive β-carbolines (compounds A-L and VI-XX) on neurite length were determined, as described above, in human SH-SY5Y neuroblastoma cells after 14 days. Table 1 summarizes die results.

Induction on Growth Factor Formation:

Next, it was investigated, whether the substances could induce the formation of nerve growth factors in human SH-SY5Y neuroblastoma cell. After 2 and 14 days the cells were harvested and the expression of the target gene and the house keeping gene was determined via reverse transcriptase-PCR. FIG. 5 shows the mean values of three independent experiments for nerve growth factors, for which a regenerating effect on injured hair cells is known.

FIG. 4A shows the relative gene expression of BDNF (brain-derived neurotrophic factor) in human SH-SY5Y cells. The transcription of BNDF after two days was stimulated only at the highest concentration (110 µM) of LE-02 (9-methyl-β-carboline), whereas after 14 days of exposition the lower concentrations of 30 and 50 µM induced stimulation. Such a shift was also found for 9-fluoroethyl-β-carboline (substance no. 559; after two days: stimulation by 70 and 90 µM; after 14 days by 30 and 50 µM). In contrast, 6-methoxy-9-methyl-9H-β-carboline (substance no. 513 in FIG. 4A) led to an enormous, dose-dependent increase of BDNF transcription.

FIG. 4B shows the relative gene expression of cerebellin-1 precursor protein (CBLN). Cerebellin-1 precursor protein was increased only after two days exposure to 9-fluoroethyl-β-carboline. After 14 days of exposure, all tested β-carbolines increased CBLN expression. Lower concentrations of the test substances had a stronger effect than higher concentrations with the exception of 9-fluoroethyl-β-carboline, showing roughly the same stimulation at all investigated concentrations. Cerebellin-1 9-fluoroethyl-β-carboline showed similar effects on CBLN expression as well as on neurite length (see FIG. 3D).

FIG. 4C shows the relative gene expression of GDNF (glial cell line-derived neurothrophic factor). At individual concentrations, 14 days of exposure led to a stimulation of up to three times.

NGF (nerve growth factor) and NPY (neuropeptide Y) are growth factors, generally necessary for the survival of nerve cells. The elimination of their biosynthesis leads to nerve cell death. They allow the differentiation of e.g. synapse formation, which is indispensable for adaptation to new situations, such as new background noises, new melodies and so on. These growth factors also make it possible and regulate the renewed outgrowth of damaged nerve cells extensions hence allow the reintegration of the newly grown cell extensions into the present nerve tracts and circuits. They are an important part of the natural repair mechanism for acute and chronic hearing injuries.

FIG. 4D shows the relative gene expression of NGF (nerve growth factor). After 14 days of exposure the gene expression was increased by 20 to 50 times. Again, the lower concentrations were far more effective in increasing NGF.

FIG. 4E shows the relative gene expression of NPY (Neuropeptide Y). After 14 days of exposure the gene expression was increased by 1.3 to 4 times. In case of 9-methyl-β-carboline and 9-fluoroethyl-β-carboline the lower concentrations were more effective than the higher concentrations.

The effects of the other inventive β-carbolines (compounds A-L and VI-XX) on the gene expression of BDNF, GDNF, NGF and NPY were determined, as described above, in human SH-SY5Y neuroblastoma cells after 2 and 14 days. Table 2 summarizes these results.

TABLE 2

Further β-carbolines in comparison to 9-methyl-β-carboline

| 9-methyl-β-carboline | standard |
|---|---|
| compound C | ± |
| compound D | + |
| compound (XI) | ± |
| compound (XII) | + |
| compound E | ± |
| compound F | ± |
| compound G | ± |
| compound H | ± |
| harman | − |
| compound J | − |
| compound K | − |
| compound L | ± |
| compound (XVI) | − |
| compound (XVII) | ± |
| compound (VII) | ± |
| compound B | − |
| compound (XIII) | ± |
| compound (XIV) | − |
| compound A | − |
| compound (XX) | ± |
| compound (VIII) | − |
| compound I | − |
| compound (XV) | ± |
| compound (IX) | − |
| compound (X) | ± |

+: marginally better than 9-methyl-β-carboline
±: equal to 9-methyl-β-carboline
−: marginally worse than 9-methyl-β-carboline Investigations on Activation of Intracellular Cascades for Clarification of Those Transcription Factors that Substantially Stimulate Differentiation by Gene Transcription:

The effects of β-carbolines on several intracellular cascades were investigated. Of them it is known, that at their respective ends, several transcription factors are formed in the cell nucleus, that in turn activate the transcription of a group of further genes. The dual luciferase method was used. One luciferase served as transfection control, whereas the second is coupled to the appropriate specific binding sequence of the DNA.

FIG. 5 shows a dose-dependent, activating effect of 9-methyl-β-carboline, 9-fluoroethyl-β-carboline and 6-methoxy-9-methyl-9H-β-carboline on the formation of the transcription factor CREB, up to ten times of the level in the control cells SH-SY5Y (three independent experiments, 48 h incubation).

These findings clearly show that the examined inventive β-carbolines have pro-differentiating effects. The induction on expression of several growth factors, from which it is known, that they can act neuroprotective and in several injury models also neuroregenerative, proves a therapeutic effect of the active substances. The effects are mediated by activation of intracellular cascades that activate transcription factors. These transcription factors transcribe a group of genes that inter alia code for growth factors.

Example 29

Pharmacokinetic Experiments in an Animal Model

In this example, 9-methyl-β-carboline is delivered locally to the recess in front of the membrane of the round window. β-Carboline can diffuse from the recess to the perilymph (liquid, which protects the sensory cells) of the inner ear (cochlea) and semicircular canal of the equilibrium organ through the round window.

Local application avoids unwanted effects, which are to be expected in case of systemic application, because, on the one hand, a comparatively high dose is required and, on the other hand, the risk of unwanted effects is increased empirically for chronic application such as is required in case of deafness and, possibly, vertigo. Therefore, prerequisite for use of the substance is that it mainly diffuses through the membrane of the round window.

To test this, 9-methyl-β-carboline-HCl (9-Me-BC) was dissolved in sterile phosphate-buffered saline (PBS) and was then infused continuously to the membrane of the round window of guinea pigs by an osmotic mini-pump at a flow rate of 0.5 μL/h for up to 10 hours. Thus, infusion took place into the middle ear and, therefore, outside the cochlea of the inner ear, whereby the tympanic membrane was not damaged. After three hours, 5 μL of perilymph were obtained from the apex, the tip of the cochlea, i.e. the part of the cochlea distanced most from the membrane of the round window, by a previously implanted cannula. The sample was diluted and was separated immediately by high-pressure liquid chromatography (HPLC) without further processing; and the natural fluorescence of β-carboline was determined by a fluorescence detector. The experiment was repeated with a second guinea pig and identical conditions but the sample was obtained after a 10-hour infusion. Perilymph was obtained from a third guinea pig that had not been treated with 9-Me-BC before (blank value control).

In a second series, 20 μg of 9-Me-BC were applied into the perilymph straight through the membrane of the round window, i.e. intra-cochlear. After three hours and after 20 hours in case of another animal, perilymph was obtained and analysed as described above. Results are depicted in FIG. 6 together with a calibration series. The calibration series shows that 10 pg of 9-Me-BC can be detected reliably by this method. A single maximum, which represents 9-Me-BC, can be seen after 7 minutes in the upper chromatogram of FIG. 6. Clearly, no further maximum is to be seen; thus, 9-Me-BC is not degraded. Furthermore, the chromatograms clearly show that 9-Me-BC penetrates the membrane of the round window.

Both chromatograms of the middle row show that 9-Me-BC is still present after 20 hours in case of straight application to the perilymph. This is of eminent significance for a therapeutic use. Furthermore, these chromatograms show that 9-Me-BC is neither degraded nor does it decay during this long period. Thus, 9-Me-BC is chemically and metabolically inert (nota bene, nanograms are detected by the upper rows and nanograms in the middle row; therefore, the so-called injection peaks can be seen in the left chromatogram of the middle and lower rows and the noise of the base line).

A chromatogram, which shows that no 9-Me-BC is present in the perilymph of an untreated animal, is pictured to the left of the lower row (blank value control). The untreated animal is an animal whereby only the surgical steps, as for the other guinea pigs, were performed but no 9-Me-BC was applied. Results are very advantageous in comparison to other substances (dexamethasone, gentamicin, 2-methyl-thiazolidin-2,4-dicarboxylic acid [tialin]) in terms of the therapy.

Medicaments, which are used for treatment of diseases of one system, are also effective for diseases of the other system because sensory cells of the hearing organ, i.e. hair cells, behave very similar to the sensory cells of the equilibrium organ.

Example 30

Prophylaxis of Hearing Damages in an Animal Model

A solution containing β-carboline was infused continuously into the recess in front of the membrane of the round window of guinea pigs by a osmotic mini-pump for three days. The following β-carbolines were tested individually in this experiment: 9-methyl-β-carboline, compounds XI, XII, XVIII, XIX as well as C to L.

Then, a standard dose of gentamicin and etacrynic acid was injected intravenously into guinea pigs. Gentamicin and etacrynic acid damage the inner ear. Typically, they are used as toxins to induce deafness in such studies. The infusion was continued for further two days. Then, the electrophysiological activity of the nerve cells of the brain stem, which transmit the impulses of the inner ear, was deduced after acoustic irradiation of the ear with 2, 4, 8, and 20 Hz. The non-β-carboline-treated ear served as intraindividual control (Prieskorn D M, Miller J M. Technical report: chronic and acute intracochlear infusion in rodents. Hear Res, 2000; 140 (1-2): 212-215). Moreover, animals were infused with 9-Me-BC only but not with gentamicin as a further control.

The measured electrophysiological activity of the nerve cells of the acoustic nerve (hearing threshold) served as a measure of the degree of therapeutic effect of the used β-carbolines on the inner ear. As can be learned from Table 3, the used β-carbolines show the increase in electrophysiological activity of the nerve cells of the acoustic nerve. It can be concluded from this that β-carbolines are useful for the treatment of hearing damages, vertigo, and vestibular disorders.

TABLE 3

Effects of different β-carbolines on the inner ear in comparison to 9-methyl-β-carboline

| 9-methyl-β-carboline | standard |
|---|---|
| fluoroethyl-BC (XIX) | + |
| 9-Me-6-MeO—BC (XVIII) | ± |
| compound C | + |
| compound D | − |
| compound (XI) | ± |
| compound (XII) | + |
| compound E | − |
| compound F | ± |
| compound G | + |
| compound H | + |
| harman I | − |
| compound J | ± |
| compound K | ± |
| compound L | + |
| compound (XVI) | − |
| compound (XVII) | − |
| compound (VII) | − |
| compound B | − |
| compound (XIII) | ± |
| compound (XIV) | − |
| compound A | − |
| compound (XX) | ± |
| compound (VIII) | ± |
| compound I | − |
| compound (XV) | − |
| compound (IX) | − |
| compound (X) | ± |

+: marginally better than 9-methyl-β-carboline
±: equal to 9-methyl-β-carboline
−: marginally worse than 9-9-methyl-β-carboline

Example 31

Formulation of 9-methyl-β-carboline for Topical Application

A gel formulation with 50 μM 9-methyl-β-carboline for topical application consists of 0.7 weight percent hyaluronic acid in phosphate buffered saline solution, such as Hylumed Sterile from Genzyme Corp, with a concentration of 50 μM 9-methyl-β-carboline.

Example 32

Formulation of 9-methyl-β-carboline for Topical Application

For topical application of 9-methyl-β-carboline in form of ear drops, a solution of 3 mg/ml 9-methyl-β-carboline is prepared in purified water with use of one of the following adjuvants: benzalconiumchloride, sodium acetate x3 H$_2$O, acetic acid, mannitol (Ph. Eur.), sodium edentate (Ph. Eur.) and hydrochloric acid/sodium hydroxide (for pH adjustment).

Example 33

Formulation of 9-methyl-β-carboline for Topical Application 100 mg 9-methyl-β-carboline is added to a solution of 0.1 mg butylhydroxyanisol (Ph. Eur.) in 939.9 mg glycerol. The resulting solution can be applied topically in the ear. Optionally, penetration enhancers, such as DMSO can be added.

Example 34

Formulation of 9-methyl-β-carboline for Oral Application

This example concerns the formulation for a film-coated tablet with 12.5 mg 9-methyl-β-carboline. The tablet core consists of:

| | |
|---|---|
| 9-methyl-β-carboline | 12.50 mg |
| Cellulose, micro crystalline | 103.25 mg |
| Croscarmellose-Na | 6.24 mg |
| Silizium dioxide, colloidal | 1.25 mg |
| Talcum | 1.25 mg |
| Magnesium stearate | 0.50 mg |
| Total weight | 125.0 mg |

The tablet core is coated with 5 mg hydroxypropylmethylcellulose (HPMC), for example with Opadry or Sepifilm. The resulting film tablet has a total weight of 130 mg and contains, besides the mentioned adjuvants, 12.5 mg 9-methyl-β-carboline.

Example 35

Formulation of 9-methyl-β-carboline for Oral Application

This example concerns the formulation for a film-coated tablet with 50.0 mg 9-methyl-β-carboline. The tablet core consists of:

| | |
|---|---|
| 9-methyl-β-carboline | 50.0 mg |
| Cellulose, micro crystalline | 413.0 mg |
| Croscarmellose-Na | 25.0 mg |
| Silizium dioxide, colloidal | 5.0 mg |
| Talcum | 5.0 mg |
| Magnesium stearate | 2.0 mg |
| Total weight | 500.0 mg |

The tablet core is coated with 20 mg HPMC, for example with Opadry or Sepifilm. The resulting film tablet has a total weight of 520 mg and contains, besides the mentioned adjuvants, 50 mg 9-methyl-β-carboline.

Example 36

Formulation of 6-methoxy-9-methyl-9H-β-carboline for Oral Application

This example concerns the formulation for a film-coated tablet with 50.0 mg 6-methoxy-9-methyl-9H-β-carboline. The tablet core consists of:

| | |
|---|---|
| 6-methoxy-9-methyl-9H-β-carboline | 50.0 mg |
| Cellulose, micro crystalline | 413.0 mg |
| Croscarmellose-Na | 25.0 mg |
| Silizium dioxide, colloidal | 5.0 mg |
| Talcum | 5.0 mg |
| Magnesium stearate | 2.0 mg |
| Total weight | 500.0 mg |

The tablet core is coated with 20 mg HPMC, for example with Opadry or Sepifilm. The resulting film tablet has a total weight of 520 mg and contains, besides the mentioned adjuvants, 50 mg 6-methoxy-9-methyl-9H-β-carboline.

Example 37

Formulation of 9-fluoroethyl-β-carboline for Oral Application

This example concerns the formulation for a film-coated tablet with 37.5 mg 9-fluoroethyl-β-carboline. The tablet core consists of:

| | |
|---|---|
| 9-fluoroethyl-β-carboline | 37.50 mg |
| Cellulose, micro crystalline | 309.75 mg |
| Croscarmellose-Na | 18.75 mg |
| Silizium dioxide, colloidal | 3.75 mg |
| Talcum | 3.75 mg |
| Magnesium stearate | 1.5 mg |
| Total weight | 375.00 mg |

The invention claimed is:

1. A method for treatment of hearing damages, vertigo and vestibular disorders in a subject comprising administering to the subject who would benefit from such treatment a therapeutically effective amount of one or more compounds of the general formula (I)

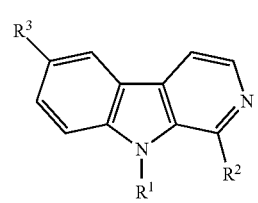

wherein
$R^1$ stands for —$R^{12}$;
$R^2$ and $R^3$ represent independently of each other the following moieties: —$R^7$, —$R^8$, —H, —OH, —O$R^7$, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$—Ph, —OCPh$_3$, —F, —Cl, —Br, —I, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$—N(C$_3$H$_7$)$_2$, —N(cyclo-C$_3$H$_5$)$_2$, —N[CH(CH$_3$)$_2$]$_2$, —N[C(CH$_3$)$_3$]$_2$, —OCF$_3$, —OC$_2$F$_5$,
$R^7$, $R^8$ and $R^{12}$ represent independently of each other the following moieties: CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, cyclo-C$_3$H$_5$, cyclo-C$_4$H$_7$, cyclo-C$_5$H$_9$, cyclo-C$_6$H$_{11}$, cyclo-C$_7$H$_{13}$, cyclo-C$_8$H$_{15}$, —Ph, —CH$_2$—Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH₂, —CH₂—CH=CH₂, —C(CH₃)=CH₂, —CH=CH—CH₃, —C₂H₄—CH=CH₂, —C₇H₁₅, —C₈H₁₇, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —CH₂—CH₂—CH₂—OCH₃, —C₂H₄—CH(CH₃)—CH=CH₂, —CH₂—CH(CH₃)—CH₂—CH=CH₂, —CH₂NH₂, —CH(CH₃)—C₂H₄—CH=CH₂, —C₂H₄—CH=C(CH₃)₂, —C₂H₄—C(CH₃)=CH—CH₃, —CH₂—CH(CH₃)—CH=CH—CH₃, —CH(CH₃)—CH₂—CH=CH—CH₃, —CH₂OH, —CH₂—CH=CH—CH(CH₃)₂, —CH₂—CH=C(CH₃)—C₂H₅, —CH₂—CH₂—CH₂NH₂, —CH₂—C(CH₃)=CH—C₂H₅, —CH(CH₃)—CH=CH—C₂H₅, —CH₂—CH₂NH₂, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —CH(CH₃)—CH₂—C(CH₃)=CH₂, —CH(CH₃)—CH(CH₃)—CH=CH₂, —CH₂—CH₂—CH₂OH, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—CH=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —CH=CH—C₂H₄—CH=CH₂, —CH₂—CH=CH—CH=CH—CH₃, —CH=CH—CH₂—CH=CH—CH₃, —CH=CH—CH₂—CH₂—OCH₃, —CH=CH—CH=CH—C₂H₅, —CH₂—CH=CH—C(CH₃)=CH₂, —CH₂—CH₂OH, —CH₂—CH=C(CH₃)—CH=CH₂, —CH₂—C(CH₃)=CH—CH=CH₂, —CH₂—OCH₃, —CH(CH₃)—CH=CH—CH=CH₂, —CH=CH—CH₂—C(CH₃)=CH₂, —CH=CH—CH(CH₃)—CH=CH₂, —CH=C(CH₃)—CH₂—CH=CH₂, —C(CH₃)=CH—CH₂—CH=CH₂, —CH=CH—CH=C(CH₃)₂, —CH=CH—C(CH₃)=CH—CH₃, —CH=CH—C(CH₃)=CH—CH₃, —C(CH₃)=CH—CH=CH—CH₃, —CH=C(CH₃)—CH=CH—CH₃, —C(CH₃)=C(CH₃)—CH=CH₂, —CH=C(CH₃)—C(CH₃)=CH₂, —C(CH₃)=CH—C(CH₃)=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C≡C—C(CH₃)₃, —C₂H₄—CH(CH₃)—C≡CH, —CH₂—CH(CH₃)—CH₂—C≡CH, —CH₂—C≡C—CH(CH₃)₂, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C₁₄H₂₉, —CH₂—CH₂—N(CH₃)₂;

and pharmacological acceptable salts, enantiomers, diastereomers or racemates of the afore-mentioned compounds.

2. The method of claim 1 wherein one or more of the compounds have the general formula (V)

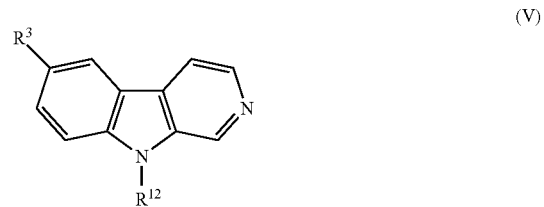

(V)

wherein the moieties $R^{12}$ and $R^3$ have the meaning described in claim 1.

3. The method of claim 1 wherein one or more of the compounds are selected from the group consisting of: 9-methyl-9H-β-carboline, 6-methoxy-9-iso-propyl-9H-β-carboline, 9-[(1Z)-1-methylprop-1-enyl]-9H-β-carboline, 1-chloro-9-[(1Z,3E)-2-methylpenta-1,3-dienyl]-9H-β-carboline, 9-methyl-6-propoxy-9H-β-carboline, 9-cyclopropyl-6-methoxy-9H-β-carboline, 6-trifluormethoxy-9-methyl-9H-β-carboline, 6-dimethylamino-9-methyl-9H-β-carboline, 1-methoxy-6-chloro-9-methyl-9H-β-carboline, 1,9-dimethyl-9H-β-carboline, 1-isopropyl-6,9-dimethyl-9H-β-carboline, 6,9-dimethyl-9H-β-carboline, 6-methoxy-9-methyl-9H-β-carboline, 9-(2-fluorethyl)-9H-β-carboline and 9-allyl-9H-β-carboline.

4. The method of claim 1, wherein the hearing damages, vertigo and vestibular disorders are in particular acute hearing loss, acute acoustic trauma, explosion trauma, labyrinthine deafness due to chronic noise exposure, presbycusia, trauma during implantation of inner ear prosthesis (insertion trauma), vertigo due to diseases of the inner ear vestibular disorders as a symptom of Menière's disease, tinnitus and hearing damages due to antibiotics and cytostatics.

5. Method for prophylaxis of hearing damages and tinnitus of a patient due to antibiotics and cytostatics comprising the administration of compounds of the general formula (I)

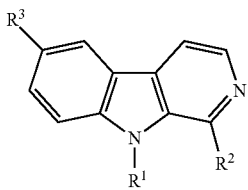

(I)

wherein
R¹ stands for —R¹²;
R² and R³ represent independently of each other the following moieties: —R⁷, —R⁸, —H, —OH, —OR⁷, —OCH₃, —OC₂H₅, —OC₃H₇, —O-cyclo-C₃H₅, —OCH(CH₃)₂, —OC(CH₃)₃, —OC₄H₉, —OPh, —OCH₂—Ph, —OCPh₃, —F, —Cl, —Br, —I, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂—N(C₃H₇)₂, —N(cyclo-C₃H₅)₂, —N[CH(CH₃)₂]₂, —N[C(CH₃)₃]₂, —OCF₃, —OC₂F₅, R⁷, R⁸ and R¹² represent independently of each other the following moieties: —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-C₅H₉, cyclo-C₆H₁₁, cyclo-C₇H₁₃, cyclo-C₈H₁₅, —Ph, —CH₂—Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂-CH=CH₂, —C(CH₃)=CH₂, —CH=CH—CH₃, —C₂H₄—CH=CH₂, —C₇H₁₅, —C₈H₁₇, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH₂—CH=CH₂, —C(CH₃)=CH—CH=CH₂, —CH=CH—C(CH₃)=CH₂, —CH=CH—CH=CH—CH₃, —CH₂—CH(CH₃)=CH—CH₂, —C₂H₄—C(CH₃)=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)₂—CH=CH₂, —CH(CH₃)—C(CH₃)=CH₂, —C(CH₃)=C(CH₃)₂, —C(CH₃)₂—CH=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —CH₂—CH₂—CH₂—OCH₃, —C₂H₄—CH(CH₃)—CH=CH₂, —CH₂—CH(CH₃)—CH₂—CH=CH₂, —CH₂NH₂, —CH(CH₃)—C₂H₄—CH=CH₂, —C₂H₄—CH=C(CH₃)₂, —C₂H₄—C(CH₃)=CH—CH₃, —CH₂—CH(CH₃)—CH=CH—CH₃, —CH(CH₃)—CH₂—CH=CH—CH₃, —CH₂OH, —CH₂—CH—CH(CH₃)₂, —CH₂—CH=CH—CH(CH₃)₂, —CH₂—CH=C(CH₃)—C₂H₅, —CH₂—CH₂NH₂, —CH₂—C(CH₃)=CH—C₂H₅, —CH₂—CH₂NH₂, —CH=CH—CH₂—CH(CH₃)₂, —CH=CH—CH(CH₃)—C₂H₅, —CH=C(CH₃)—C₃H₇, —C(CH₃)=CH—C₃H₇, —C(CH₃)=CH—C₃H₇, —CH₂—CH(CH₃)—C(CH₃)=CH₂, —CH(CH₃)—CH₂—C(CH₃)=CH₂, —CH(CH₃)—CH(CH₃)—CH=CH₂, —CH₂—CH₂—CH₂OH, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂, —CH—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —CH₂—CH₂—CH=CH—CH=CH₂, —CH=CH—CH₂—CH=CH₂, —CH=CH—C₂H₄—CH=CH₂, —CH₂—CH=CH—CH=CH—CH₃, —CH=CH—CH₂—CH=CH—CH₃, —CH₂—CH₂—OCH₃, —CH=CH—CH=CH—C₂H₅, —CH₂—CH=CH—C(CH₃)=CH₂, —CH₂—CH₂OH, —CH₂—CH=C(CH₃)—CH=CH₂, —CH₂—C(CH₃)=CH—CH=CH₂, —CH₂—OCH₃, —CH(CH₃)—CH=CH—CH=CH₂, —CH=CH—CH₂—C(CH₃)=CH₂, —CH=CH—CH(CH₃)—CH=CH₂, —CH=CH—CH=CH₂, —CH=C(CH₃)—CH₂—CH=CH₂, —C(CH₃)=CH—CH₂—CH=CH₂, —CH=CH—CH=C(CH₃)₂, —CH=CH—C(CH₃)=CH—CH₃, —CH=C(CH₃)—CH=CH—CH₃, —C(CH₃)=CH—CH=CH—CH₃, —CH=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C≡C—C(CH₃)₃, —C₂H₄—CH(CH₃)—C≡CH, —CH₂—CH(CH₃)—CH₂—C≡CH, —CH₂—C≡C—CH(CH₃)₂, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—C≡CH, —CH(C₃H₇)—C≡CH, —C(CH₃)(C₂H₅)—C≡CH, —C₁₄H₂₉, —CH₂—CH₂—N(CH₃)₂;

as well as pharmacological acceptable salts, enantiomers, diastereomers as well as racemates of the aforementioned compounds.

* * * * *